(12) United States Patent
Morohashi

(10) Patent No.: US 8,955,972 B2
(45) Date of Patent: Feb. 17, 2015

(54) OPHTHALMOLOGIC APPARATUS

(71) Applicant: Canon Kabushiki Kaisha, Tokyo (JP)

(72) Inventor: Kazuya Morohashi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/904,704

(22) Filed: May 29, 2013

(65) Prior Publication Data

US 2013/0321766 A1    Dec. 5, 2013

(30) Foreign Application Priority Data

Jun. 1, 2012 (JP) ................................. 2012-126193

(51) Int. Cl.
*A61B 3/14* (2006.01)
*A61B 3/00* (2006.01)

(52) U.S. Cl.
USPC .......................................... 351/206; 351/246

(58) Field of Classification Search
USPC ................................................ 351/200–246
See application file for complete search history.

(56) References Cited

U.S. PATENT DOCUMENTS

| | | | |
|---|---|---|---|
| 6,337,993 B1 | 1/2002 | Kishida et al. | |
| 6,655,805 B2 | 12/2003 | Fujieda | |
| 7,527,379 B2 * | 5/2009 | Yamaguchi et al. | 351/205 |
| 7,635,186 B2 * | 12/2009 | Kobayashi et al. | 351/221 |
| 7,736,001 B2 | 6/2010 | Tanaka et al. | |
| 8,469,514 B2 | 6/2013 | Utsunomiya | |
| 8,506,081 B2 | 8/2013 | Matsumoto | |
| 8,596,785 B2 | 12/2013 | Imamura et al. | |
| 8,646,915 B2 | 2/2014 | Nozato | |
| 8,708,489 B2 | 4/2014 | Utagawa | |
| 2001/0056239 A1 | 12/2001 | Ono | |
| 2007/0216866 A1 | 9/2007 | Kobayashi et al. | |
| 2009/0303428 A1 | 12/2009 | Tendler | |
| 2012/0019780 A1 | 1/2012 | Nozato | |
| 2012/0033180 A1 | 2/2012 | Pieri et al. | |
| 2013/0321765 A1 | 12/2013 | Yuasa | |
| 2013/0321766 A1 | 12/2013 | Morohashi | |
| 2013/0321767 A1 | 12/2013 | Hirose | |
| 2013/0321768 A1 | 12/2013 | Utagawa | |
| 2013/0321769 A1 | 12/2013 | Kusumoto | |
| 2013/0321771 A1 | 12/2013 | Yuasa | |
| 2014/0063507 A1 | 3/2014 | Borycki et al. | |

FOREIGN PATENT DOCUMENTS

JP 2010-259543 A 11/2010

* cited by examiner

*Primary Examiner* — Mohammed Hasan
(74) *Attorney, Agent, or Firm* — Canon U.S.A., Inc. IP Division

(57) ABSTRACT

An ophthalmologic apparatus includes an aberration measurement unit configured to measure aberration caused by a subject's eye by using a return beam of a first measuring beam from the subject's eye, a correction unit configured to correct aberration of a return beam of a second measuring beam from the subject's eye caused by the subject's eye based on the aberration measured by the aberration measurement unit, a first acquisition unit configured to obtain a first image of the subject's eye by using the aberration-corrected return beam of the second measuring beam from the subject's eye, and a control unit configured to enter one of the first measuring beam and the second measuring beam into the subject's eye while limiting entry of the other measuring beams into the subject's eye.

16 Claims, 8 Drawing Sheets

OPHTHALMOLOGIC APPARATUS

BACKGROUND OF THE INVENTION

1. Field of the Invention

The present invention relates to an ophthalmologic apparatus.

2. Description of the Related Art

A scanning laser ophthalmoscope (SLO), which is an ophthalmologic apparatus using a principle of a confocal laser microscope, performs raster scanning for, for example, a fundus of a subject's eye with a laser that is a measuring beam, and obtains a planar image based on the intensity of its return beam from the subject's eye with high resolution at a high speed. Hereinafter, an apparatus that captures such a planar image may be referred to as a SLO apparatus.

There is known a technology for measuring aberration caused by the subject's eye by a wavefront sensor in real time, and correcting the aberration caused by the subject's eye by a wavefront correction device. Japanese Patent Application Laid-Open No. 2010-259543 discusses an adaptive optics SLO (hereinafter, may be referred to as AOSLO apparatus) having an adaptive optical system for correcting the aberration by the wavefront correction device. This technology enables a planar image of high lateral resolution to be obtained. The technology discussed in Japanese Patent Application Laid-Open No. 2010-259543 prohibits, when alignment of a fundus image of a wide field angle is not proper, emission of illumination beams from a light source for obtaining the planar image of high lateral resolution and a light source for measuring the aberration.

However, when turning ON/OFF of the light source is controlled, it takes longer time from turning-ON of the light source to stabilization of the emitted beam, and as a result, it causes a problem of longer inspection time. When beams from a plurality of light sources are simultaneously applied to the subject's eye without controlling turning ON/OFF of the light sources, a beam amount obtained by integrating the amounts of beams emitted from the light sources must be a level having no safety problem. In other words, as compared with a case where the subject's eye is irradiated with a beam from one light source, when the subject's eye is irradiated with beams from the plurality of light sources, the amounts of beams from the respective light sources must be kept low because of safety problems, thus causing reduction of image quality.

SUMMARY OF THE INVENTION

The present invention is directed to an ophthalmologic apparatus capable of preventing image quality from being deteriorated while securing safety and preventing inspection time from becoming longer.

Not limited to this objective, the present invention is also directed to an ophthalmologic apparatus capable of achieving operation effects obtained by exemplary embodiments of the present invention described below and not achieved by the conventional art.

According to an aspect of the present invention, an ophthalmologic apparatus includes a first light source configured to emit a first measuring beam, a second light source configured to emit a second measuring beam, a first limitation unit disposed in an optical path connecting the first light source with a subject's eye and configured to limit entry of the first measuring beam into the subject's eye, a second limitation unit disposed in an optical path connecting the second light source with the subject's eye and configured to limit entry of the second measuring beam into the subject's eye, an aberration measurement unit configured to measure aberration caused by a subject's eye by using a return beam of the first measuring beam from the subject's eye, a correction unit configured to correct aberration of the return beam of the second measuring beam from the subject's eye caused by the subject's eye based on the aberration measured by the aberration measurement unit, a first acquisition unit configured to obtain a first image of the subject's eye by using the aberration-corrected return beam of the second measuring beam from the subject's eye, and a control unit configured to allow, in lit states of the first light source and the second light source, one of the first measuring beam and the second measuring beam to enter into the subject's eye while limiting entry of the other measuring beam into the subject's eye by controlling the first limitation unit and the second limitation unit According to another aspect of the present invention, an ophthalmologic apparatus includes a plurality of light sources configured to emit measuring beams, a shutter disposed in an optical path connecting each of the plurality of light sources with a subject's eye, and a control unit configured to allow, in lit states of the plurality of light sources, one of the plurality of measuring beams emitted from the plurality of light sources to enter into the subject's eye while limiting entry of the other measuring beams into the subject's eye by controlling opening/closing of the shutter.

According to yet another aspect of the present invention, an ophthalmologic apparatus includes a first illumination optical system configured to illuminate a subject's eye with a first measuring beam emitted from a first light source, a second illumination optical system configured to illuminate the subject's eye by scanning the subject's eye with a second measuring beam emitted from a second light source, a third illumination optical system configured to illuminate the subject's eye by scanning the subject's eye with a third measuring beam emitted from a third light source, a first shutter disposed in the first illumination optical system, a second shutter disposed in the second illumination optical system, a third shutter disposed in the third illumination optical system, a measurement optical system configured to measure aberration caused by the subject's eye by using a return beam of the first measuring beam from the subject's eye, a first imaging optical system configured to capture an image of the subject's eye by using a return beam of the second measuring beam from the subject's eye, a second imaging optical system configured to capture an image of the subject's eye by using a return beam of the third measuring beam from the subject's eye to determine an imaging position of the first imaging optical system, a correction unit disposed in the first imaging optical system and configured to correct aberration of the return beam of the second measuring beam from the subject's eye by using the aberration measured by the measurement optical system, and a control unit configured to control, in lit states of the first light source, the second light source, and the third light source, opening/closing of the first shutter, the second shutter, and the third shutter to open one of the first shutter, the second shutter, and the third shutter while closing the other two shutters.

According to the present invention, reduction of image quality can be prevented while safety is secured, and inspection time can be prevented from becoming longer.

Further features of the present invention will become apparent from the following detailed description of exemplary embodiments with reference to the attached drawings.

DESCRIPTION OF THE EMBODIMENTS

Various exemplary embodiments, features, and aspects of the invention will be described in detail below with reference to the drawings. The present invention is not limited to the exemplary embodiments described below. Various changes and modifications can be made within the scope of the present invention.

In an exemplary embodiment, as an ophthalmologic apparatus, an AOSLO apparatus according to the present invention will be described. The AOSLO apparatus, which includes an adaptive optical system, captures a high lateral resolution planar image (hereinafter, may be referred to as an AOSLO image) of a fundus of a subject's eye.

For the purpose of assisting obtaining of the AOSLO image, the AOSLO apparatus includes a WFSLO unit for capturing a wide field angle planar image (WFSLO image). The AOSLO apparatus further includes an anterior eye portion observation unit for grasping the incident position of a measuring beam, and a fixation lamp unit for guiding a line of sight to adjust an imaging place.

In the AOSLO apparatus of the present exemplary embodiment, optical aberration caused by the subject's eye is corrected by using a spatial light modulator to obtain a planar image. Thus, a good planar image with reduced influence of a diopter of the subject's eye and the optical aberration caused by the subject's eye can be obtained.

In the present exemplary embodiment, the AOSLO device includes the adaptive optical system to capture the high lateral resolution planar image. However, the adaptive optical system is unnecessary as long as the configuration of the optical system can realize high resolution.

<Overall Configuration of Apparatus>

Figure 1A:
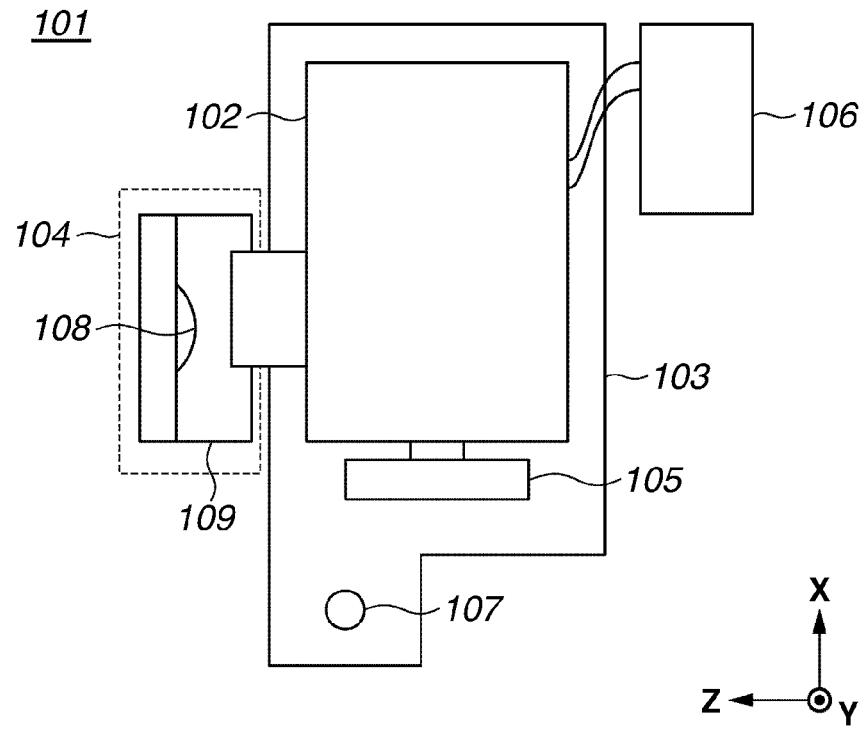
FIGS. 1A and 1B illustrate an example of an entire configuration of an AOSLO apparatus according to an exemplary embodiment of the present invention.
Figure 1B:
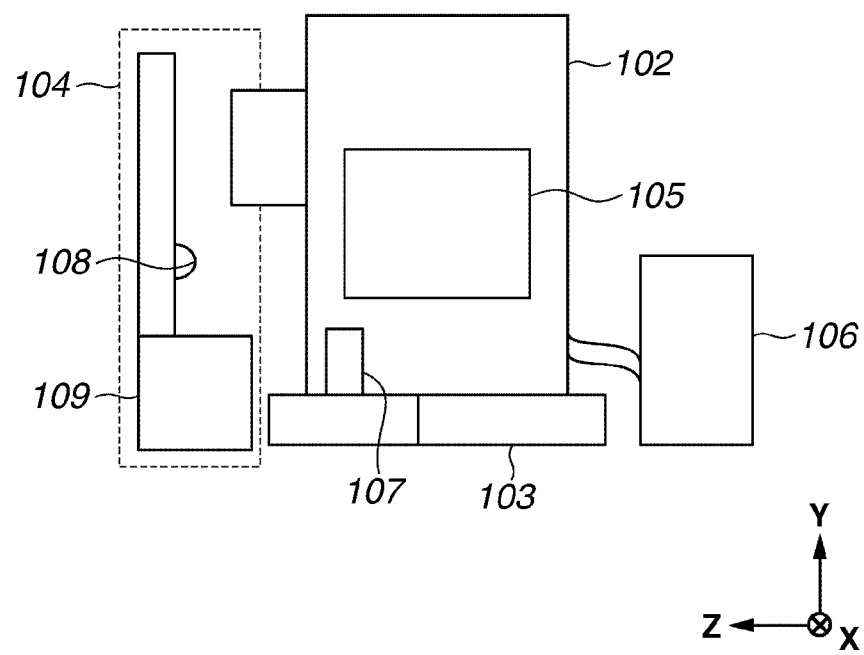

Referring to FIGS. 1A and 1B, a schematic configuration of an AOSLO apparatus 101 according to the present exemplary embodiment will be described. FIGS. 1A and 1B illustrate an example of an entire configuration of the AOSLO apparatus 101 according to the present exemplary embodiment. FIG. 1A is a top view of the AOSLO apparatus 101 of the present embodiment, and FIG. 1B is a side view of the AOSLO apparatus 101 of the present exemplary embodiment. In the present exemplary embodiment, the AOSLO apparatus 101 seen from a face receiver 104 side is defined as a front.

The AOSLO apparatus 101 includes a head unit 102, a stage unit 103, a face receiver 104, a liquid crystal monitor 105, a control PC 106, and a joystick 107.

The head unit 102 includes a unit for capturing an image of, for example, a subject's eye, and a main optical system. The included optical system will be described in detail below. In the present exemplary embodiment, the head unit 102 is mounted on the stage unit 103.

The stage unit 103 moves the head unit 102 in horizontal and vertical directions according to an examiner's operation of the joystick 107. For example, the head unit 102 can be moved in the horizontal direction (X and Z directions) by tilting the joystick 107, and in the vertical direction (Y direction) by rotating the joystick 107.

A face of the subject can be rested on the face receiver 104, and a position of the subject's eye can be adjusted by moving the face receiver 104. Specifically, the face receiver 104 includes a jaw receiver 108 on which a jaw is rested, and a jaw receiver driving unit 109 for moving the jaw receiver 108 by an electric stage.

The liquid crystal monitor 105, which can display various pieces of information, displays, for example, an operation screen of the AOSLO apparatus 101. The liquid crystal monitor 105 corresponds to an example of a display unit. In the present exemplary embodiment, the liquid crystal display is used for a monitor. It is not limited thereto, and any type of a monitor can be used as long as it can display information. The liquid crystal monitor 105 may have a touch panel function.

The control PC 106 controls the entire AOSLO apparatus 101.

The joystick 107 receives an instruction from the examiner. For example, the head unit 102 can be moved in the horizontal direction by tilting the joystick 107, and in the vertical direction by rotating the joystick 107. When the liquid crystal monitor 105 has a touch panel function, and the head unit 102 can be moved via the touch panel, there is no need to provide any joystick 107.

The liquid crystal monitor 105 is provided on the side face of the head unit 102. However, it is not limited to this, and the liquid crystal monitor 105 can be provided at another position such as the rear surface of the head unit 102. Further, the position of the liquid crystal monitor 105 can be fixed or movable. The control PC 106 is provided outside the head unit 102. However, it is not limited to this, and the control PC 106 can be provided in the head unit 102 or the stage unit 103. The joystick 107 is provided on the side face of the head unit 102. However, it is not limited to this, and the joystick 107 can be provided at another position such as the rear surface of the head unit 102.

<Configuration of Optical System>

Figure 2:
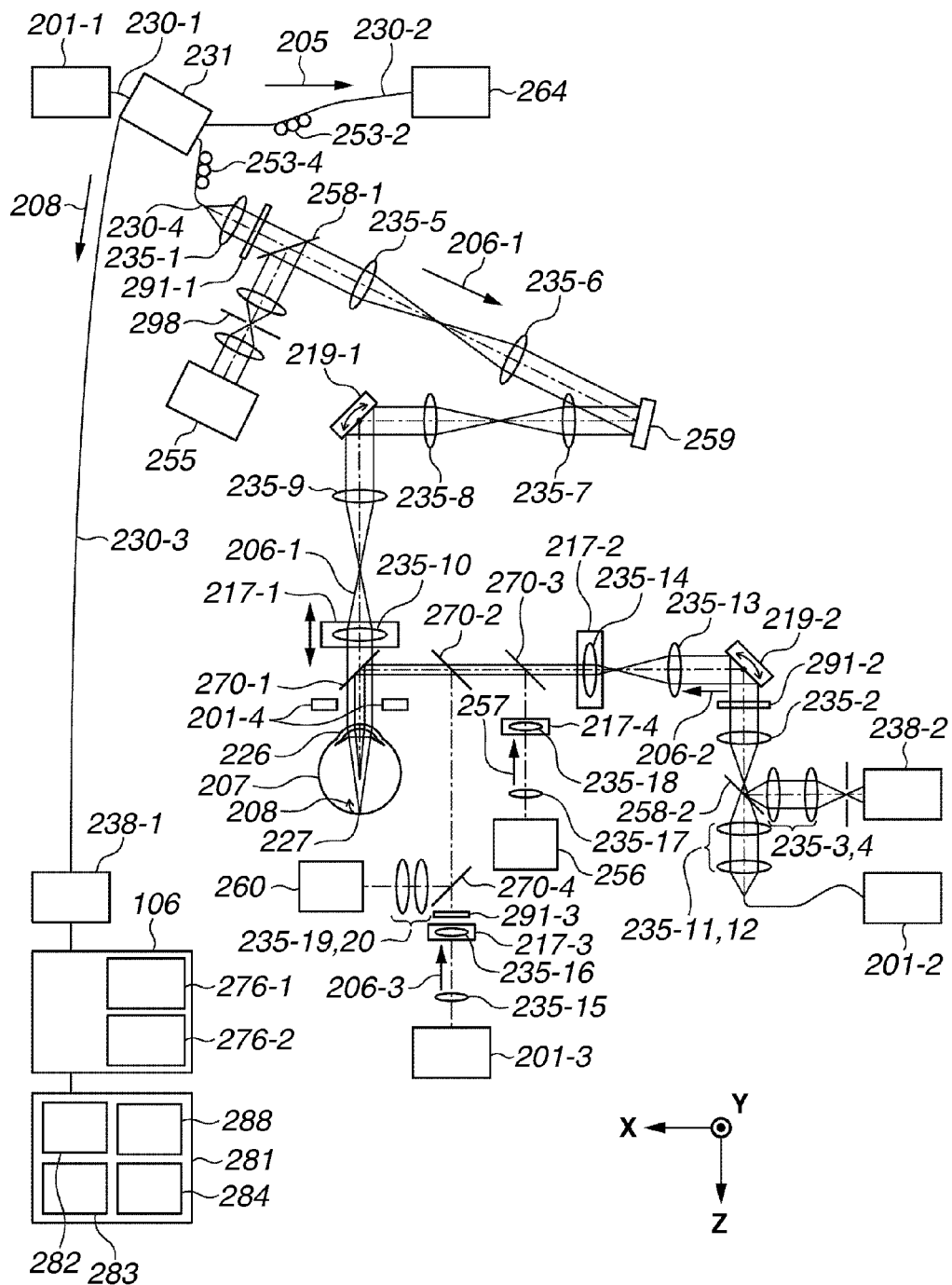
FIG. 2 illustrates an example of a configuration of an optical system of an AOSLO apparatus according to an exemplary embodiment of the present invention.

Next, referring to FIG. 2, the optical system included in the head unit 102 will specifically be described. The entire optical system illustrated in FIG. 2 does not need to be included in the head unit 102. For example, the optical system illustrated in FIG. 2 can be included in the head unit 102 and the stage unit 103. FIG. 2 illustrates an example of a configuration of the optical system of the AOSLO apparatus 101 according to the present exemplary embodiment.

In the present exemplary embodiment, the entire optical system is configured by a refractive optical system mainly using lenses. However, the optical system can be configured by a reflective optical system using spherical mirrors in place of the lenses.

The optical system illustrated in FIG. 2 includes an AOSLO unit, a beacon unit, a WFSLO unit, a fixation lamp unit, and an anterior eye portion observation unit.

The AOSLO unit includes a light source 201-1, single mode fibers 230-1, 230-3, and 230-4, an optical fiber 230-2, a photocoupler 231, polarization controllers 253-2 and 253-24, and a shutter 291-1. The shutter 291-2 corresponds to an example of a first limitation unit disposed in an optical path connecting a second light source with the subject's eye, and configured to limit entry of the first measuring beam into the subject's eye. Further, the AOSLO unit includes lenses 235-1, 235-5, 235-6, 235-7, 235-8, 235-9, and 235-10, a beam splitter 258-1, a spatial light modulator 259, and an X-Y scanner 219-1. The AOSLO unit includes a dichroic mirror 270-1, an electric stage 217-1, a light amount measurement apparatus 264, and a detector 238-1.

The beacon unit includes a light source 201-3, lenses 235-5, 235-6, 235-7, 235-8, 235-9, 235-10, 235-15, and 235-16, an X-Y scanner 219-1, a spatial light modulator 259, and a pinhole 298. The beacon unit further includes a shutter 291-3, dichroic mirrors 270-1, 270-2, and 270-4, electric stages 217-1 and 271-3, a beam splitter 258-1, and a wavefront sensor 255. The shutter 291-3 corresponds to an example of a first limitation unit disposed in an optical path connecting the first light source with the subject's eye and configured to limit entry of the second measuring beam into the subject's eye.

The WFSLO unit includes a light source 201-2, lenses 235-2, 235-3, 235-4, 235-11, 235-12, 235-13, and 235-14, a beam splitter 258-2, and an X-Y scanner 219-2. The WFSLO unit further includes an electric stage 217-2, dichroic mirrors 270-1, 270-2, and 270-3, a shutter 291-2, and a detector 238-2.

The fixation lamp unit includes a fixation lamp 256, lenses 235-17 and 235-18, dichroic mirrors 270-1, 270-2, and 270-3, and an electric stage 217-4.

The anterior eye portion observation unit includes an anterior eye portion illumination light source 201-4, dichroic mirrors 270-1, 270-2, and 270-4, lenses 235-19 and 235-20, and a charge-coupled device (CCD) camera 260.

<AOSLO Unit>

The AOSLO unit obtains an AOSLO image.

First, the light source 201-1 will be described. The light source 201-1 is a super luminescent diode (SLD) that is a representative low-coherent light source. As an example, a center wavelength of a beam emitted from the light source 201-1 is 840 nm, and a band width (half value full width) is 50 nm. A value of the center wavelength is determined in view of, for example, losses caused by beam absorption of the subject's eye (crystal lens or corpus vitreum). Generally, losses caused by beam absorption are smaller at near 840 nm than that at a proximate wavelength. The light source 201-1 corresponds to an example of the second light source for emitting the second measuring beam. In this case, the low-coherent light source is selected to obtain a planar image having low speckle noise. The SLD is selected as the light source. However, any type of a light source can be used as long as it can emit a low-coherent beam, and an amplified spontaneous emission (ASE) or the like can also be used.

For the wavelength, near-infrared light is suitable in view of eye measurement. Further, a shorter wavelength is desirable because it affects horizontal resolution of the obtained planar image and, in this case, for example, the wavelength is 840 nm. However, other wavelengths can be selected depending on measured portions of the observation target.

The beam emitted from the light source 201-1 is divided into a reference beam 205 and a measuring beam 206-1 at a rate of 90:10 via the single mode fiber 230-1 and the photocoupler 231. More specifically, the beam emitted from the light source 201-1 is divided into the reference beam 205 and the measuring beam 206-1 by the photocoupler 231. The branch ratio by the photocoupler 231 is not limited to this value.

<Reference Beam 205>

Next, an optical path of the reference beam 205 will be described.

The reference beam 205 divided by the photocoupler 231 enters into the light amount measurement apparatus 264 via the optical fiber 230-2 including a polarization controller 253-2 for controlling beam polarization. The light amount measurement apparatus 264 is used for measuring an amount of the reference beam 205 and monitoring an amount of the measuring beam 206-1. For example, when a measured value of the light amount measurement apparatus 264 exceeds a predetermined threshold value, it is determined that a safe beam amount is exceeded, and the control PC 106 limits entry of the beam emitted from the light source 201-1 into the subject's eye.

<Measuring Beam 206-1>

Next, an optical path of the measuring beam 206-1 will be described.

The measuring beam 206-1 divided by the photocoupler 231 is guided to the lens 235-1 via the single mode fiber 230-4 including a polarization controller 253-4 for controlling beam polarization, and changed to be a parallel beam having, for example, a diameter of 4 mm by the lens 235-1. The value of the beam diameter is only an example, and thus in no way limitative. Then, the measuring beam 206-1 reaches the beam splitter 258-1 via the shutter 291-1. The shutter 291-1 can control whether to allow the beam emitted from the light source 201-1 to enter into the subject's eye 207.

The measuring beam 206-1 passes through the beam splitter 258-1 and the lenses 235-5 and 235-6 to enter into the spatial light modulator 259. The beam splitter 258-1 transmits the beam output from the light source 201-1 to the subject's eye 207 and a return beam from the subject's eye 207 by the light source 201-1 while reflecting to the wavefront sensor 255 a beam emitted from the light source 201-3 and returned from the subject's eye 207. In other words, the beam splitter 258-1 has characteristics of transmitting beams of wavelengths 800 to 880 nm while reflecting beams of other wavelengths.

In the present exemplary embodiment, the reflective spatial light modulator is used as the aberration correction device. However, a transmissive spatial light modulator or a variable shape mirror may be used.

The spatial light modulator 259 is controlled by the control PC 106 via a spatial light modulator driver 288 in the driver unit 281. In other words, the spatial light modulator driver 288 is electrically connected to the spatial light modulator 259. The driver unit 281 illustrated in FIG. 2 is provided outside the control PC 106. However, the driver unit 281 may be disposed in the control PC 106.

Then, the measuring beam 206-1 is modulated by the spatial light modulator 259, and passed through lenses 235-7 and 235-8 to enter into the mirror of the XY scanner 219-1. For simplicity, the XY scanner 219-1 is one mirror. Actually, however, two mirrors are arranged close to each other as an X scanner and a Y scanner, and raster scanning is performed on a retina 227 vertically to the optical axis. A center of the measuring beam 206-1 is adjusted to coincide with a mirror rotational center of the XY scanner 219-1.

The X scanner scans the measuring beam 206-1 in a direction parallel to a paper surface, and a resonance scanner is used. For example, a driving frequency of the X scanner is about 7.9 kHz. The Y scanner scans the measuring beam 206-1 in a direction vertical to the paper surface, and a Galvano scanner is used. For example, a driving waveform is a saw-tooth wave, a frequency is about 32 Hz, and a duty ratio is 16%. The driving frequency of the Y scanner is an important parameter for determining a frame rate of capturing AOSLO image.

The XY scanner 219-1 is controlled from the control PC 106 via an optical scanner driver 282 in a driver unit 281. In other words, the optical scanner driver 282 is electrically connected to the XY scanner 219-1.

The measuring beam 206-1 scanned by the XY scanner 219-1 is guided to the subject's eye 207 that is an observation target via the lenses 235-9 and 235-10 and the dichroic mirror 270-1. In other words, the AOSLO unit corresponds to an example of a second illumination optical system for illuminating the subject's eye by scanning the subject's eye with the second measuring beam emitted from the second light source.

The lenses 235-9 and 235-10, which are optical systems for scanning the retina 227, play roles of scanning the retina 227 with the measuring beam 206-1 with a pupil being center of the subject's eye 207 set as a supporting point.

A diameter of the measuring beam 206-1 is 4 mm. However, the beam diameter may be larger to obtain an optical image of higher resolution, and a beam diameter may be smaller than 4 mm when high resolution is not necessary. That is, the beam diameter is not limited to 4 mm.

An electric stage 217-1 can be moved in an illustrated arrow direction to move a position of the accompanying lens 235-10, thereby adjusting a focus.

The electric stage 217-1 is controlled from the control PC 106 via an electric stage driver 283 in the driver unit 281. In other words, the electric stage driver 283 is electrically connected to the electric stage 217-1. Adjusting the position of the lens 235-10 enables focusing of the measuring beam 206-1 on a predetermined layer of the retina 227 of the subject's eye 207 to perform observation. The apparatus can even deal with refraction abnormality in the subject's eye 207.

The measuring beam 206-1 that has passed through the lens 235-10 enters into the subject's eye via the dichroic mirror 270-1.

The dichroic mirror 270-1 transmits the beam output from the light source 201-1 to the subject's eye and a beam emitted from the light source 201-1 and returned from the subject's eye. The dichroic mirror 270-1 reflects a beam output from the light source 201-2 to the subject's eye, a beam emitted from the light source 201-2 and returned from the subject's eye, and a beam emitted from the anterior eye portion illumination light source 201-4 and returned from the subject's eye. The dichroic mirror 270-1 reflects a beam from the fixation lamp 256. Further, for example, the dichroic mirror 270-1 reflects a half and transmits a half of a beam output from the light source 201-3 to the subject's eye and a beam emitted from the light source 201-3 and returned from the subject's eye. A ratio of reflection and transmission is not limited to 1:1. In other words, the dichroic mirror 270-1 has characteristics of transmitting beams of wavelengths 800 to 880 nm while reflecting a half and transmitting a half of beams of wavelengths 750 to 770 nm. The dichroic mirror 270-1 enables separation of the beams emitted from the light source 201-1 and the light source 201-3 from the other light sources.

The measuring beam 206-1, which has entered into the subject's eye 207, becomes a return beam 208 by reflection or scattering from the retina 227 to reversely travel on the optical path, and is guided again to the photocoupler 231. Then, the return beam reaches the detector 238-1 via the single mode fiber 230-3. In other word, the AOSLO unit corresponds to an example of a first imaging optical system for imaging the subject's eye by using the return beam of the second measuring beam from the subject's eye. The spatial light modulator 259 corresponds to an example of a correction unit disposed in the first imaging optical system and configured to correct aberration of the return beam of the second measuring beam from the subject's eye by using the aberration measured by the measurement optical system. For the detector 238-1, for example, an avalanche photodiode (APD) or a photomultiplier tube (PMT) that is a high-speed and high-sensitive optical sensor is used. However, the detector is not limited to these. The detector 238-1 converts the intensity of the return beam 208 into a voltage, and the control PC 106 forms a planar image of the subject's eye 207 by using this voltage signal. In other words, the detector 238-1 corresponds to an example of a first acquisition unit for obtaining a first image of the subject's eye by using the aberration corrected return beam of the second measuring beam from the subject's eye.

<WFSLO Unit>

Next, the WFSLO unit will be described. The WFSLO unit obtains a WFSLO image. The WFSLO unit has a configuration basically similar to that of the AOSLO unit, and thus description of overlapped portions will be omitted.

The WFSLO unit includes a light source 201-2. The light source 201-2 is a SLD as in the case of the AOSLO unit. A center wavelength of a beam emitted from the light source 201-2 is 920 nm, and a band width is 20 nm. The light source 201-2 corresponds to an example of a third light source for emitting a third measuring beam. The SLD is selected as a type of the light source. However, any type of a light source can be used as long as it can emit a low-coherent beam, and amplified spontaneous emission (ASE) can also be used. The wavelength and the band width of the beam emitted from the light source 201-2 are not limited to these values. Other values can be employed.

An optical path of a measuring beam 206-2 emitted from the light source 201-2 will be described. The measuring beam 206-2 emitted from the light source 201-2 is guided to the subject's eye 207 that is an observation target via the shutter 291-2, the lens 235-2, the lenses 235-11 to 235-14, the beam splitter 258-2, the XY scanner 219-2, and the dichroic mirrors 270-1 to 270-3. In other words, the WFSLO unit corresponds to an example of a third illumination optical system for illuminating the subject's eye by scanning the subject's eye with a third measuring beam emitted from a third light source. The shutter 291-2 can control whether to allow the beam emitted from the light source 201-3 to enter into the subject's eye 207.

The beam splitter 258-2 transmits the beam output from the light source 201-2 to the subject's eye while reflecting to the detector 238-2 a beam emitted from the light source 201-2 and returned from the subject's eye. In other words, the WFSLO unit corresponds to an example of a second imaging optical system for imaging the subject's eye by using the return beam of the third measuring beam from the subject's eye to determine an imaging position of the first imaging optical system.

The dichroic mirror 270-2 transmits the beam output from the light source 201-2 to the subject's eye, a beam emitted from the light source 201-2 and returned from the subject's eye, and a beam from the fixation lamp 256. The dichroic mirror 270-2 reflects a beam output from the light source 201-3 to the subject's eye and a beam emitted from the light source 201-3 and returned from the subject's eye. The dichroic mirror 270-2 reflects a beam output from the anterior eye portion illumination light source 201-4 and returned from the subject's eye 207. In other words, the dichroic mirror 270-2 has characteristics of reflecting beams of wavelengths 700 to 880 nm while transmitting beams of other wavelengths. The dichroic mirror 270-2 enables separation of the beams emitted from the light source 201-3 and the anterior eye portion illumination light source 201-4 from the beams emitted from the light source 201-1 and the fixation lamp 256.

The dichroic mirror 270-3 transmits the beam output from the light source 201-2 to the subject's eye, the beam emitted from the light source 201-2 and returned from the subject's eye, and the beam from the fixation lamp 256. On the other hand, the dichroic mirror 270-3 reflects the beam output from the fixation lamp 256 to the subject's eye. In other words, the dichroic mirror 270-3 has characteristics of transmitting beams of wavelengths of 700 nm or longer while reflecting beams of other wavelengths. The dichroic mirror 270-3 enables separation of the beam emitted from the fixation lamp 256 from the beam emitted from the light source 201-2.

In FIG. 2, for simplicity, the XY scanner 219-2 is described as one mirror. Actually, two mirrors are arranged close to each other as an X scanner and a Y scanner, and raster scanning is performed on a retina 227 vertically to the optical axis.

The X scanner as a component of the XY scanner 219-2 scans the measuring beam 206-2 in a direction parallel to a paper surface, and a resonance scanner is used. For example, a driving frequency is about 3.9 kHz. The Y scanner scans the measuring beam 206-2 in a direction vertical to the paper surface, and a Galvano scanner is used. For example, a driving waveform is a saw-tooth wave, a frequency is about 15 Hz, and a duty ratio is 16%. The driving frequency of the Y scanner is an important parameter for determining a frame rate of the WFSLO image. The XY scanner 219-2 is controlled from the control PC 106 via the optical scanner driver 282 in the driver unit 281. In other words, the optical scanner driver 282 is electrically connected to the XY scanner 219-2.

The optical system is configured so that a diameter of the measuring beam 206-2 is 1 mm. However, the beam diameter may be larger to obtain an optical image of higher resolution, and a beam diameter may be smaller than 1 mm when high resolution is not necessary. In other words, the beam diameter is not limited to 1 mm.

The measuring beam 206-2, which has entered into the subject's eye 207, becomes a return beam 208 by reflection or scattering from the retina 227, and reaches the detector 238-2 via the dichroic mirrors 270-1 to 270-3, the lenses 235-13 and 235-14, the lenses 235-2 to 235-4, the XY scanner 219-2, and the beam splitter 258-2.

<Beacon Unit>

Next, a beacon unit that measures aberration generated by the subject's eye 207 will be described.

The beacon unit includes a light source 201-3. A center wavelength of a beam emitted from the light source 201-3 is 760 nm, and a band width is 20 nm. The light source 201-3 corresponds to the first light source for emitting the first measuring beam. The wavelength and the band width of the beam emitted from the light source 201-3 are not limited to these values. Other values can be employed.

A measuring beam 206-3 emitted from the light source 201-3 is guided to the subject's eye 207 that is an observation target via the shutter 291-3, the lenses 235-15 and 235-16, and the dichroic mirrors 270-1, 270-2, and 270-4. In other words, the beacon unit corresponds to an example of the first illumination optical system for illuminating the subject's eye by the first measuring beam emitted from the first light source. To prevent reflection from a cornea 226, the measuring beam 206-3 is deviated from, for example, the center of the subject's eye 207 to enter. The shutter 291-3 can control whether to allow the beam emitted from the light source 201-3 to enter into the subject's eye 207.

The dichroic mirror 270-4 transmits the beam output from the light source 201-3 to the subject's eye 207 while reflecting to the CCD camera 260 a beam emitted from the anterior eye portion illumination light source 201-4 and returned from the subject's eye. In other words, the dichroic mirror 270-4 has characteristics of transmitting beams of wavelengths of 750 nm or longer while reflecting beams of other wavelengths. The dichroic mirror 270-4 enables separation of the beam emitted from the anterior eye portion illumination light source 201-4 from the beam emitted from the light source 201-3.

A part of the return beam 208 by the light source 201-3 enters into the wavefront sensor 255 via the beam splitter 258-1 and the pinhole 298, and aberration of the return beam 208 generated in the subject's eye 207 is measured. In other words, the wavefront sensor 255 corresponds to an example of an aberration measurement unit for measuring aberration caused by the subject's eye by using the return beam of the first measuring beam from the subject's eye. The beacon unit corresponds to an example of a measurement optical system for measuring the aberration caused by the subject's eye by using the return beam of the first measuring beam from the subject's eye. The pinhole 298 is provided for the purpose of blocking off unnecessary beams other than the return beam 208. The wavefront sensor 255 is electrically connected to the control PC 106.

The wavefront sensor 255 is a Shack-Hartman wavefront sensor, and a measurement range is −10D to +5D. The acquired aberration is expressed by using Zernike polynomial, which indicates aberration caused by the subject's eye 207. The Zernike polynomial includes a tilt term, a defocus term, an astigmatism term, a coma term, and a trefoil term.

The lenses 235-5 to 235-10 are arranged so that the cornea 226, the XY scanner 219-1, the wavefront sensor 255, and the spatial light modulator 259 can be optically conjugate with one another. Thus, the wavefront sensor 255 can measure the aberration caused by the subject's eye 207. The spatial light modulator 259 can correct the aberration caused by the subject's eye 207.

<Fixation Lamp>

A light flux 257 from the fixation lamp 256 has a role of prompting fixation or rotation of the subject's eye 207.

Figure 3:
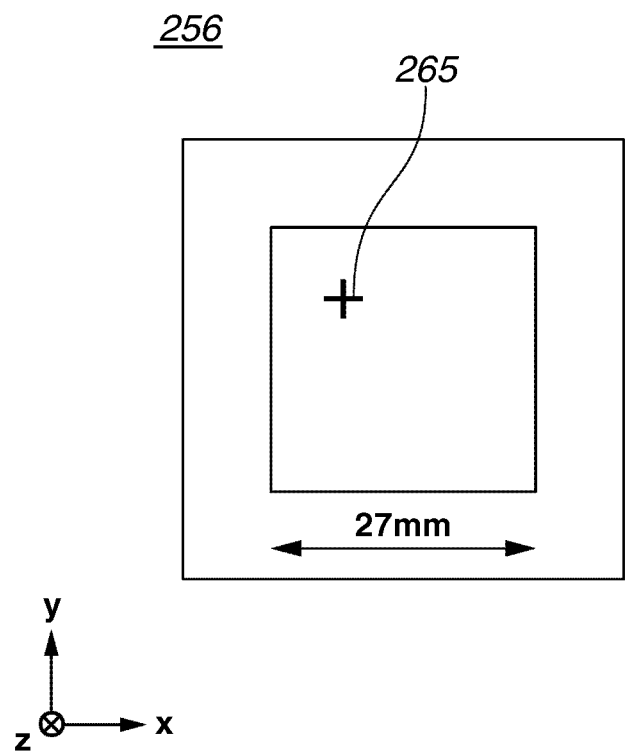
FIG. 3 illustrates an example of a fixation lamp according to an exemplary embodiment of the present invention.
Figure 4:
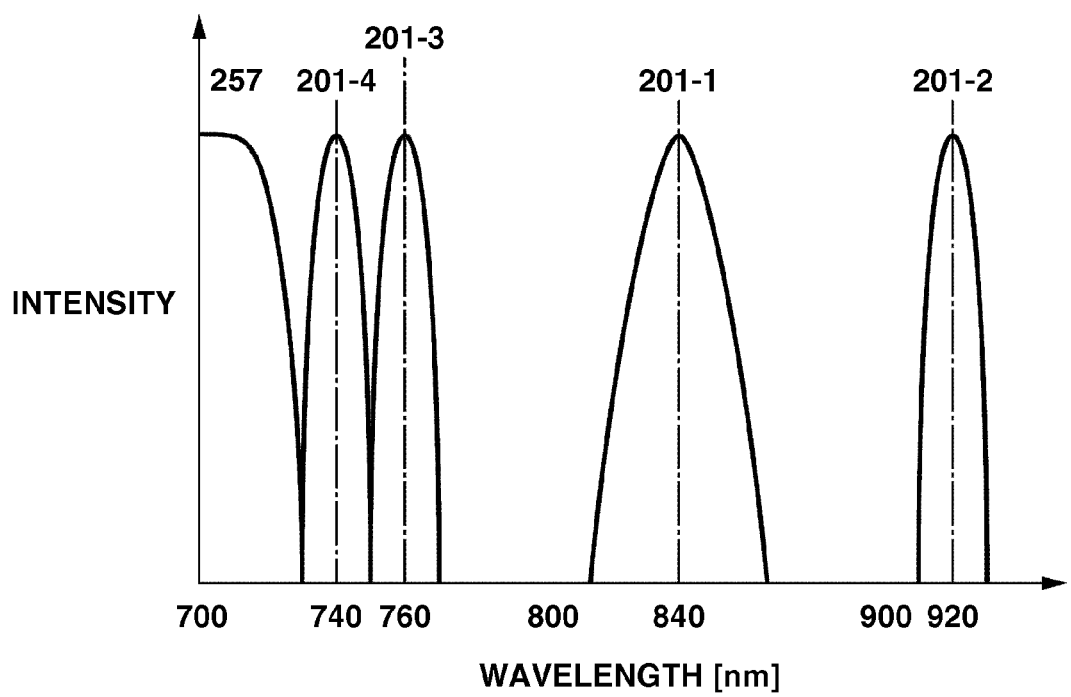
FIG. 4 illustrates an example of a wavelength distribution of a measuring beam of an AOSLO apparatus according to an exemplary embodiment of the present invention.

The fixation lamp 256, which includes a light emitting display module, has a display surface (27 mm×27 mm, 128 pixels×128 pixels) on an XY plane. A liquid crystal, an organic electroluminescence (EL), or a light emitting diode (LED) array can be used. The subject's eye 207 pays close attention to the light flux 257 from the fixation lamp 256, and accordingly fixation or rotation of the subject's eye 207 is prompted. In the display surface of the fixation lamp 256, for example, as illustrated in FIG. 3, a cross pattern is flashed to be displayed at an arbitrary lighting position 265. The light flux 257 emitted from the fixation lamp 256 is a visible beam. As illustrated in FIG. 4, a wavelength of a part of the light flux 256 (e.g., red wavelength included in the visible beam) is equal to or longer than 700 nm.

The light flux 257 from the fixation lamp 256 is guided to the retina 227 via the lenses 235-17 and 18 and the dichroic mirrors 270-1 to 270-3. The lenses 235-17 and 235-18 are arranged so that the display surface of the fixation lamp 256 and the retina 227 can be optically conjugate with each other. The fixation lamp 256 is controlled from the control PC 106 via a fixation lamp driver 284 in the driver unit 281. The fixation lamp driver 284 is electrically connected to the fixation lamp 256.

The size of the display surface of the fixation lamp 256 and the number of pixels are not limited to the aforementioned values. Other values can be employed. In the example, the cross fixation pattern is employed. However, it is not limited to this, and other shapes can be employed.

<Anterior Eye Portion Observation Unit>

Next, the anterior eye portion observation unit will be described. The anterior eye portion observation unit obtains an anterior eye portion image of the subject's eye.

The anterior eye portion observation unit 201-4 is, for example, an LED having a center wavelength of 740 nm. For example, a band width is several ten nm. The center wavelength and the band width are not limited to these values. A beam emitted from the anterior eye portion observation unit 201-4 illuminates the subject's eye 207, and its reflected beam enters into the CCD camera 260 via the dichroic mirrors 207-1, 207-2, and 207-4, and the lenses 235-19 and 235-20.

<Focus and Astigmatism Correction>

As described above, the optical system in the head unit 102 includes the AOSLO unit, the WFSLO unit, the beacon unit, the fixation lamp unit, and the anterior eye portion observation unit. The AOSLO unit, the WFSLO unit, the beacon unit, and the fixation lamp unit individually include the electric stages 217-1 to 217-4, and the four electric stages are interlockingly moved. However, when focus positions are individually adjusted, the positions can be adjusted by individually moving the electric stages.

The lens 235-10 is replaceable, and a spherical lens or a cylindrical lens can be used according to the aberration (refractive abnormality) caused by the subject's eye 207. It is not limited to one lens, but a plurality of lenses can be provided in combination.

<Shutter>

The AOSLO unit, the WFSLO unit, and the beacon unit respectively include shutters 291-1 to 291-3 on the optical paths of the light sources 201-1 to 201-3, and whether to allow a beam to enter into the subject's eye 207 can be controlled by individually blocking off beams. Opening or closing of the shutters 291-1 to 291-3 is controlled by the control PC 106 (driving/control unit 114). The shutters 291-1 to 291-3 correspond to examples of limitation units arranged in a plurality of optical paths connecting the first light source, the second light source, and the third light source with the subject's eye. In other words, the driving/control unit 114 serving as a control unit switches incidence of the measuring beam and a limitation of incidence to the subject's eye by controlling the controlling units. Specifically, the driving/control unit 114 serving as the control unit switches incidence of the measuring beam and a limitation of incidence to the subject's eye by controlling opening/closing of the shutters in the lit states of the first light source, the second light source, and the third light source. The shutters 291-1 to 291-3 correspond to examples of a first shutter, a second shutter, and a third shutter. In other words, the driving/control unit 114 corresponds to an example of a control unit for controlling opening/closing of the first shutter, the second shutter, and the third shutter to open one of the first shutter, the second shutter, and the third shutter while closing the other two in the lit states of the first light source, the second light source, and the third light source.

In the present exemplary embodiment, the shutter is used for controlling the beam entered into the subject's eye 207. However, it is not limited to this, and the beam entered into the subject's eye 207 can be controlled by changing the optical path by using a mirror or the like. The beam entered into the subject's eye 207 can be controlled by directly turning ON/OFF the light sources 201. Incidence and limitation of incidence on the subject's eye 207 can be switched by disposing an attenuation filter in place of the shutter to insert or pull it out in/from the optical path. The mirror and the filter correspond to examples of limitation units. When the limitation unit is a filter, the driving/control unit 114 serving as the control unit switches incidence of the measuring beam and a limitation of incidence to the subject's eye by inserting the filter into or pulling it out from the optical path in the lit states of the first light source, the second light source, and the third light source. Similarly, the anterior eye portion observation unit and the fixation lamp unit can be controlled by turning ON/OFF the light source 201-4 and a light-emitting display module. When the shutters 291-1 to 291-3 are used, the entry of a beam into the subject's eye 207 can be controlled while the light sources 201-1 to 201-3 are kept lit. Thus, when the incidence limitation of the measuring beam on the subject's eye 207 is released, time from turning-OFF of the light sources 201-1 to 201-3 to stable beam emission is made unnecessary, enabling quick control. Similar effects can be obtained when the mirror or the filter is used.

The opened/close states of the shutters 291-1 to 291-3 are displayed in a shutter state display region 509 of a control software screen illustrated in FIG. 7 by the display control unit 112 described below. By displaying the opened/closed state of the shutter, the examiner can clearly and easily know which of the measuring beams 206-1 to 206-3 is being applied to the subject's eye 207. As a result, certainty of an imaging operation can be improved more.

<Wavelength of Each Light Source>

FIG. 4 illustrates an example of a wavelength distribution of the light sources used for the AOSLO unit, the WFSLO unit, the beacon unit, the fixation lamp unit, and the anterior eye portion observation unit. To enable the dichroic mirrors 270-1 to 270-4 to divide the beams, different wavelength ranges are set.

To reduce dazzling of the subject's eye, the beams emitted from the light sources 201-1 to 201-4 are desirably infrared beams having wavelengths of 700 nm or longer. High image quality is not required of the light source 201-3 of the beacon unit, and only a Hartman image must be obtained. Accordingly, a beam amount can be smaller than those of the light sources 201-1 and 201-2. Thus, an influence of the wavelength of the beam emitted from the light source 201-3 on the subject is relatively low even when it is near a visible light region, and the wavelength of the beam emitted from the light source 201-3 can be near the visible light region. Sensors normally used for the detectors 238-1 and 238-2 are silicon sensors. Since sensitivity of the silicon sensor is extremely low near 1000 nm, the wavelengths of the beams emitted from the light sources 201-1 to 201-4 are desirably equal to or shorter than 1000 nm. The AOSLO apparatus 101 configured to obtain the AOSLO image uses the WFSLO image to assist obtaining of the desired AOSLO image. Thus, to obtain a desired final AOSLO image with high resolution, the wavelength of the beam emitted from the light source 201-1 is set shorter than that of the beam emitted from the light source 201-2. As described above, a center wavelength of the light source 201-1 is desirably set near 840 nm based on eye characteristics.

It is therefore useful that in the case of the AOSLO apparatus 101 for fundus observation, the beacon unit, the AOSLO unit, and the WFSLO unit are arranged in this order from the short wavelength side, and center wavelengths are separated from each other to facilitate separation by the dichroic mirror. In other words, a center wavelength of the first measuring beam is equal to or longer than 700 nm, and a center wavelength of the third measuring beam is equal to or shorter than 1000 nm.

An anterior eye portion image obtained by the light emitted from the anterior eye portion imaging light source 201-4 is used for initial alignment of the head unit 201. The alignment of the head unit 201 is performed while watching the WFSLO image. On the other hand, the beam emitted from the light source 201-3 is used for measuring aberration necessary for obtaining the desired final ALSO image with high resolution. Accordingly, since the beam amount of the light source 201-3 is set larger than that of the anterior eye portion imaging light source 201-4 to accurately measure the aberration, by setting the wavelength of the light source 201-3 longer than that of the anterior eye portion imaging light source 201-4, the aberration can be highly accurately measured while reducing a burden on the subject. In other words, a center wavelength of the fourth measuring beam is equal to or longer than 700 nm, and the center wavelength of the third measuring beam is equal to or shorter than 1000 nm. Since it is only necessary to obtain the anterior eye portion image used for the initial alignment of the head unit 201, the beam amount of the anterior eye portion imaging light source 201-4 can be smaller than those of the other light sources.

When the center wavelength of the anterior eye portion imaging light source 201-4 and the center wavelength of the light source 201-2 are switched, the center wavelength of the light source 201-2 that emits a beam to be scanned on the subject's eye approaches that of the visible beam. Consequently, the subject's eye follows a track of the beam during scanning, destabilizing fixation. Thus, the center wavelength of the anterior eye portion imaging light source 201-4 and the center wavelength of the light source 201-2 are set to be under such conditions.

An interval between the center wavelengths is desirably double or more of the sum of ½ of half-value full widths of adjacent light sources. In the present exemplary embodiment, an interval between the center wavelengths of the light source 201-1 and the light source 201-2 is 80 nm, and an interval between the center wavelengths of the light source 201-1 and the light source 201-3 is also 80 nm. Half-value full widths of the light sources 201-1 to 201-3 are respectively 50 nm, 20 nm, and 20 nm. Accordingly, double the sum of ½ of half-value full widths of the light source 201-1 and the light source 201-2 is 70 nm, double the sum of ½ of half-value full widths of the light source 201-1 and the light source 201-3 is also 70 nm, and an interval between the center wavelengths is set larger than these values. Thus, beam losses at the respective light sources can be reduced as much as possible. Hereinafter, a wavelength determination method including a wavelength determination step will specifically be described. When a wavelength distribution is generally Gaussian distribution, a width of the Gaussian distribution at a position of ½ of a peak (intensity peak) of the Gaussian distribution is a half-value full width, and intensity at a position double the half-value full width is 1/16 of the peak value of the Gaussian distribution. In other words, 95% or more of the entire beam amount is included in a portion where the width of the Gaussian distribution is less than double the half-value full width. Thus, by setting the interval between the center wavelengths double or more of the sum of ½ of half-value full widths of the adjacent light sources as described above, overlapping of the wavelengths between the light sources can be made difficult. When the interval between the center wavelengths is set double ½ of half-value full widths of the adjacent light sources, the interval between the center wavelengths can be reduced while preventing overlapping of the wavelengths between the light sources. Thus, the wavelengths can be effectively used. As a result, a wavelength as short as possible can be used to improve resolution.

In the aforementioned example, the interval between the center wavelengths is set double or more of ½ of half-value full widths of the adjacent light sources. However, the interval is not limited to this. For example, the interval between the center wavelengths can be set n times larger than the sum of 1/n of half-value full widths of the adjacent light sources, where n is a natural number. In the aforementioned example, n is 2. In other words, the interval between the adjacent center wavelengths is a value n times larger than the sum of 1/n of half-value full widths of a plurality of adjacent measuring beams. Specifically, the interval between the adjacent center wavelengths is a value n times larger than the sum of 1/n of half-value full widths of the plurality of adjacent measuring beams or more.

The wavelength width used for determining the interval between the center wavelengths may not be a half-value full width. An arbitrary wavelength width may be used. For example, a wavelength width half of the half-value full width can be used from the start to omit the division, or a wavelength width near the half-value full width may be used. In other words, the interval between the adjacent center wavelengths may be determined based on the respective wavelength widths of the plurality of adjacent measuring beams.

Further, when the interval between the adjacent center wavelengths is set double ½ of half-value full widths of the adjacent light sources, overlapping of the wavelengths between the light sources is greater than that when the interval between the center wavelengths is set double or more of the sum of ½ of half-value full widths of the adjacent light sources. In this case, an attenuation filter for reducing an influence of the wavelength overlapping is provided, and thus the influence of the wavelength overlapping can be reduced. For example, as the interval between the center wavelengths is narrower, the wavelength-overlapped portion becomes larger. Thus, an attenuation filter for attenuating wavelengths of a wider range as the interval between the center wavelengths is narrower may be used. A table associating the interval between the center wavelengths with an attenuation wavelength range is prepared, and the control PC 106 inserts or pulls out the attenuation filter (not illustrated) into/from an arbitrary position of the optical path such as before the subject's eye 207 or in each light source by referring to the table. By using such an attenuation filter, the center wavelengths can be approached more to each other. As a result, the wavelengths can be used more effectively.

An interval between the center wavelength of the light source 201-3 and the center wavelength of the light source 201-4 may be determined or may not be determined by a method similar to the aforementioned method. The interval between the center wavelengths may not be determined because the anterior eye portion image does not need accuracy as high as the other images.

FIG. 4 illustrates a difference in wavelength between the light sources, not defining intensities or spectral shapes.

<Image Formation>

Next, a configuration method of a captured image will be described.

For the beam entered into the detector 238-1, its intensity is converted into a voltage. A voltage signal obtained from the detector 238-1 is converted into a digital value at an AD board 276-1 in the control PC 106. The control PC 106 performs data processing in synchronization with an operation or a driving frequency of the XY scanner 219-1 to form an AOSLO image. A capturing speed of the AD board 276-1 is, for example, 15 MHz. Similarly, a voltage signal obtained from the detector 238-2 is converted into a digital value at an AD board 276-2 in the control PC 106, and a WFSLO image is formed by the control PC 106.

<Control PC 106>

Figure 5:
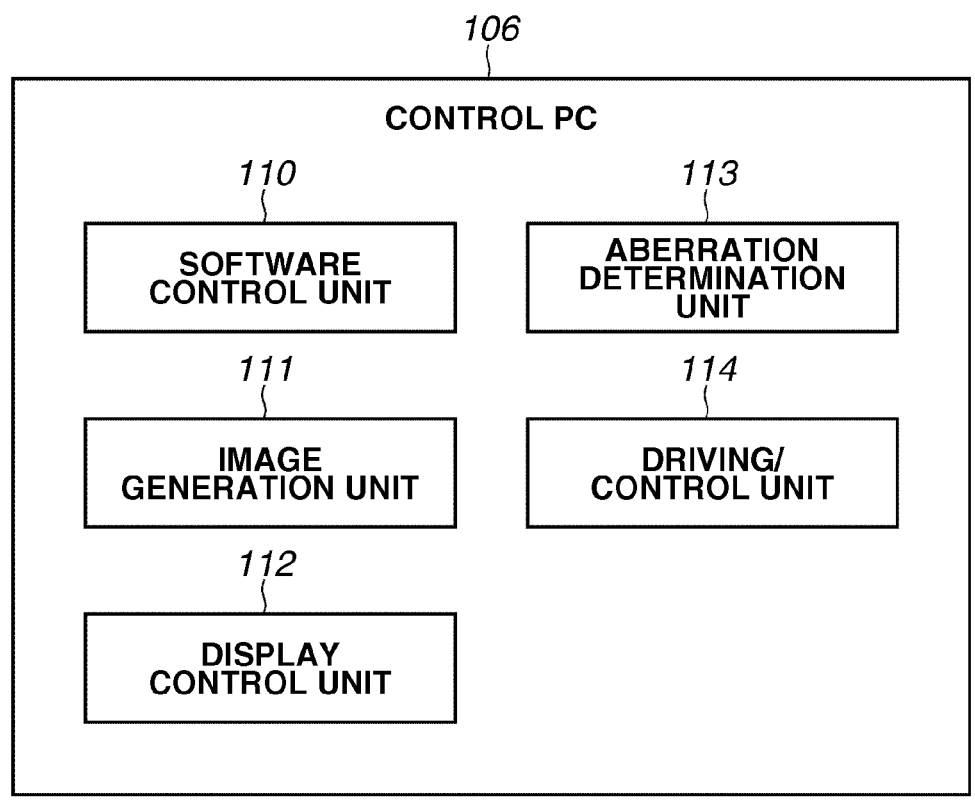
FIG. 5 schematically illustrates an example of a function of a control personal computer (PC).

An example of a function of the control PC 106 will be described. FIG. 5 schematically illustrates the example of the function of the control PC 106.

The control PC 106 functions as a software control unit 110, an image generation unit 111, a display control unit 112, an aberration determination unit 113, and a driving/control unit 114 by a processing unit such as a central processing unit (CPU) executing a predetermined program stored in a storage device such as a memory.

The software control unit 110 controls activation or stopping of measurement control software and viewer software. For example, the software control unit 110 activates the measurement control software when power of the AOSLO apparatus 101 is turned ON or when the examiner specifies a control software execution file. The software control unit 110 activates the viewer software when the examiner specifies a viewer software execution file. The software control unit 110 stops the measurement control software and the viewer software when the examiner instructs an end of the software. The control software and the viewer software may be stored in a storage unit such as a memory included in the control PC 106, or in an external storage unit communicable with the control PC 106 via wireless or wired communication.

The image generation unit 111 generates various images. For example, the image generation unit 111 generates an AOSLO image based on an output of the AD board 276-1. The image generation unit 111 generates a WFSLO image based on an output of the AD board 276-2. The image generation unit 111 generates a Hartman image based on an output of the wavefront sensor 255. The image generation unit 111 generates an anterior eye portion image based on an output of the CCD camera 260.

The display control unit 112 displays various pieces of information such as the images generated by the image generation unit 111 on the liquid crystal monitor 105. The display control unit 112 displays a graph or values of aberrations determined by the aberration determination unit 113 on the liquid crystal monitor 105.

The display control unit 112 further displays opened/closed states of the shutters 291-1 to 291-3 in a shutter state display region 509.

The information displayed in the shutter state display region 509 is not limited to the opened/closed state of the shutter. Any information indicating the incident state of the measuring beam on the subject's eye may be displayed. For example, information indicating insertion or removal of a filter in/from the optical path may be displayed when the filter is used in place of the shutter, or information indicating incidence of a measuring beam may be displayed. In other words, the display control unit 112 corresponds to an example of a display control unit for causing a display unit to display forms indicating incident states of the first measuring beam, the second measuring beam, and the third measuring beam into the subject' eye. More specifically, the display control unit 112 causes the display unit to display forms indicating opened/closed states of the shutters included in the plurality of optical paths. The display control unit 112 causes the display unit to display forms indicating inserted/pulled-out states of the shutters included in the plurality of optical paths.

The aberration determination unit 113 determines aberration caused by the subject's eye 207 based on an output of the wavefront sensor 255. Specifically, the aberration determination unit 113 determines aberration caused by the subject's eye 207 based on the Hartman image.

The driving/control unit 114 drives various movable members. Specifically, the driving/control unit 114 drives the XY scanners 219-1 and 219-2 via the optical scanner driver 282. The driving/control unit 114 drives the electric stages 217-1 to 217-4 via the electric stage driver 283. Further, the driving/control unit 114 drives the fixation lamp 256 via the fixation lamp driver 284. Specifically, the driving/control unit 114 controls movement of a lighting position 265, switching between lighting and blinking, and changing of a size or a shape. The driving/control unit 114 controls the spatial light modulator 259 via the spatial light modulator driver 288. Specifically, the driving/control unit 114 controls the spatial light modulator 259 based on the aberration determined by the aberration determination unit 113, thereby correcting the aberration caused by the subject's eye 207. More specifically, the driving/control unit 114 controls the spatial light modulator 259 to reduce the aberration. In other words, the spatial light modulator 259 corresponds to an example of a correction unit for correcting aberration, caused by the subject's eye, of the return beam of the second measuring beam from the subject's eye based on the aberration measured by the aberration measurement unit.

Further, the driving/control unit 114 drives the jaw receiver 108 via the jaw receiver driving unit 109 according to an examiner's input.

The driving/control unit 114 controls opening/closing of the shutters 291-1 to 291-3. Further, the driving/control unit 114 controls turning ON or OFF of the light source. The driving/control unit 114 corresponds to an example of a control unit for allowing, by controlling the first limitation unit and the second limitation unit in the lit states of the first light source and the second light source, to enter one of the first measuring beam and the second measuring beam into the subject's eye while limiting entry of the other measuring beams into the subject's eye.

<Imaging Procedure>

Figure 6:
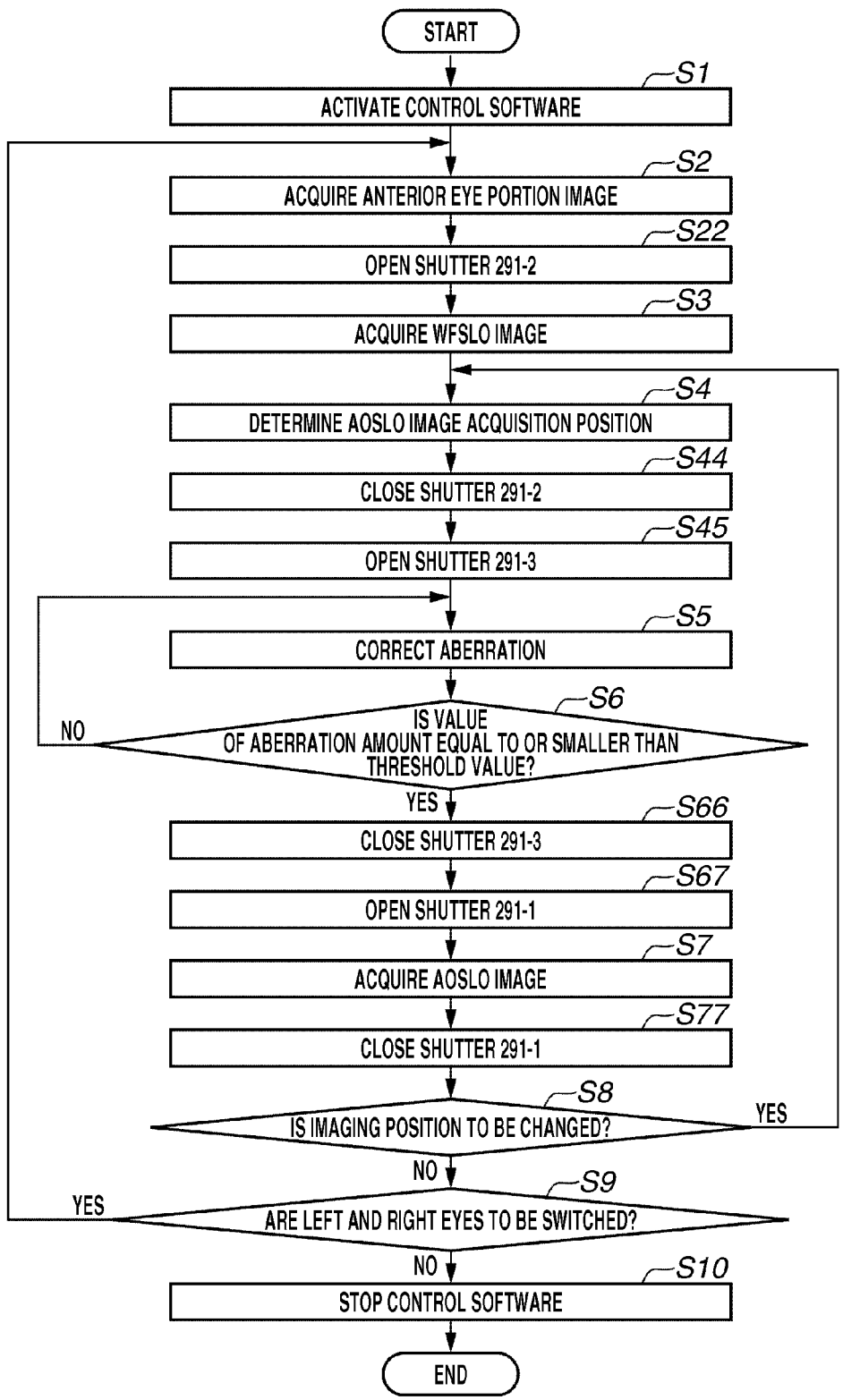
FIG. 6 is a flowchart illustrating an example of an imaging procedure by an AOSLO apparatus according to an exemplary embodiment of the present invention.

Next, referring to FIGS. 6 and 7, an imaging procedure in the AOSLO apparatus 101 of the present exemplary embodiment will be described. FIG. 6 is a flowchart illustrating an example of an operation of the AOSLO apparatus according to the present exemplary embodiment. FIG. 7 illustrates an example of a control screen of the AOSLO apparatus 101 displayed on the liquid crystal monitor 105 according to the present exemplary embodiment.

Hereinafter, each step of the flowchart will be described in detail. In an initial state, the shutters 291-1 to 291-3 are all closed.

When power is turned ON for the AOSLO apparatus 101 including the control PC 106, each processing of the AOSLO apparatus 101 is started.

In step S1, when the power of the AOSLO apparatus 101 including the control PC 106 is turned ON, the software control unit 110 activates the measurement control software. When the measurement control software is activated, the display control unit 112 displays the control software screen illustrated in FIG. 7 on the liquid crystal monitor 105. The subject sets a face on the face receiver 104 after the measurement control software has been activated.

An example of the control screen illustrated in FIG. 7 will be described. A screen configuration of the control software illustrated in FIG. 7 is only an example, and thus in no way limitative. In other words, arrangement or the like of the control screen can be arbitrarily changed.

Figure 7:
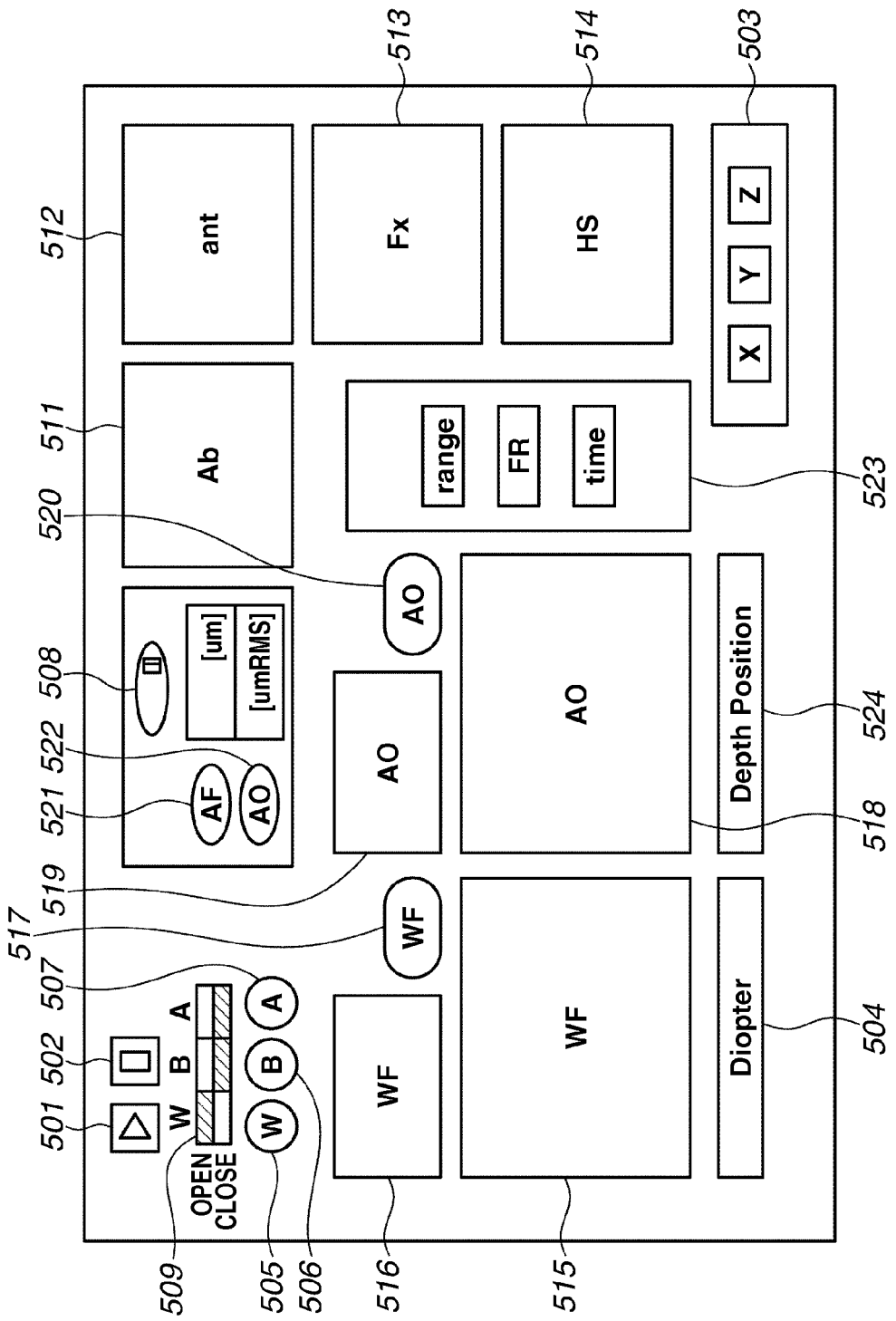
FIG. 7 illustrates an example of a configuration of a control software screen of an AOSLO apparatus according to an exemplary embodiment of the present invention.

The control screen illustrated in FIG. 7 includes an execution button 501, a stop button 502, an electric stage button 503, a focus adjustment button 504, a WFSLO measurement button 505, an aberration measurement button 506, and an AOSLO measurement button 507.

The control screen illustrated in FIG. 7 includes an aberration correction pause button 508, a shutter state display region 509, an aberration display region 511, an anterior eye portion display region 512, a fixation lamp position display region 513, a wavefront display region 514, and a WFSLO display region 515.

The control screen illustrated in FIG. 7 includes a WFSLO intensity display region 516, a WFSLO recording button 517, an AOSLO display region 518, an AOSLO intensity display region 519, an AOSLO recording button 520, and an autofocus button 521.

The control screen illustrated in FIG. 7 further includes an aberration correction button 522, an imaging condition setting button 523, and a depth adjustment button 524.

After the execution button 501 is selected (e.g., clicked) by an instruction unit such as a mouse, the driving/control unit 114 turns ON the anterior eye portion illumination light source 201-4, and a beam emitted from the anterior eye portion illumination light source 201-4 enters into the subject's eye 207. Then, the display control unit 112 displays an anterior eye portion image generated based on an output of the CCD camera 260 in the anterior eye portion display region 512.

When the execution button 501 is selected, the control PC 106 may display a screen for selecting or registering patient information on the liquid crystal monitor 105. In this case, after the patient information is selected or registered, the anterior eye portion illumination light source 201-4 may be lit, and the display control unit 112 may display an anterior eye portion image in the anterior eye portion display region 512. The selection by the instruction unit is not limited to clicking. When the liquid crystal monitor 105 has a touch panel function, the examiner may perform selection by touching the monitor.

When the stop button 502 is selected, the software control unit 110 stops the control software.

The electric stage movement button 503 includes an X stage movement button, a Y stage movement button, and a Z stage movement button. When the electric stage movement button 503 is selected, the driving/control unit 114 moves the jaw receiver 108 via the jaw receiver driving unit 109. For example, each of the X stage movement button, the Y stage movement button, and the Z stage movement button is a slider, and the driving/control unit 114 moves the jaw receiver 108 according to a moving amount and a moving direction of the slider. For example, when the Y stage movement button is selected, the driving/control unit 114 moves the jaw receiver 108 in a Y direction. Similarly, the driving/control unit 114 moves the jaw receiver 108 in an X direction and a Y direction according to selected buttons. The electric stage movement button 503 is not limited to the slider. Any other form can be employed as long as driving can be instructed to the jaw receiver 108.

For example, the focus adjustment button 504 is a slider. The driving/control unit 114 drives the lenses 235-10, 235-14, 235-16, and 235-18 according to a moving amount and a moving direction of the slider. The focus adjustment button 504 is not limited to the slider. Any other form can be employed as long as driving can be instructed to the lenses 235-10, 235-14, 235-16, and 235-18.

When the WFSLO measurement button 505 is selected, the control PC 106 allows the beam emitted from the light source 201-1 to enter into the subject's eye. Specifically, a state where entry of the beams emitted from the light sources 201-1 to 201-3 into the subject's eye is limited before selection of the WFSLO measurement button 505 is changed to a state where the beam emitted from the light source 201-2 enters into the subject's eye. This switching is carried out by the driving/control unit 114, for example, turning ON the turned-OFF light source 201-2 or removing the shutter inserted into the optical path connecting the subject's eye with the light source 201-2.

When the aberration measurement button 506 is selected, the driving/control unit 114 limits entry of the beam emitted from the light source 201-2 into the subject's eye. The entry of the emitted beam into the subject's eye 207 is limited by, for example, closing the shutter 291-2 in the optical path connecting the subject's eye 207 with the light source 201-2 or turning OFF the light source 201-2. When the aberration measurement button 506 is selected, the control PC 106 allows the beam emitted from the light source 201-3 to enter into the subject's eye 207. Specifically, a state where entry of the beams emitted from the light sources 201-1 and 201-3 into the subject's eye is limited before the aberration measurement button 506 is selected is changed to a state where the beam emitted from the light source 201-3 enters into the subject's eye. This switching is carried out by the driving/control unit 114 by, for example, turning ON the turned-OFF light source 201-3 or opening the shutter 291-3 inserted into the optical path connecting the subject's eye 207 with the light source 201-3. Either one of the limitation of the entry of the beam emitted from the light source 201-2 into the subject's eye 207 and the permission of the entry of the beam emitted from the light source 201-3 into the subject's eye 207 may be executed first, or both may be simultaneously executed. However, it is desired that to limit the increase of a beam amount entered into the subject's eye 207 as much as possible, after the entry of the beam emitted from the light source 201-2 into the subject's eye 207 is limited, the entry of the beam emitted from the light source 201-3 into the subject's eye 207 is allowed.

When the AOSLO measurement button 507 is selected, the driving/control unit 114 limits entry of the beam emitted from the light source 201-3 into the subject's eye. The entry of the emitted beam into the subject's eye 207 is limited by, for example, closing the shutter 291-3 of the optical path connecting the subject's eye 207 with the light source 201-3 or turning OFF the light source 201-3. When the AOSLO measurement button 507 is selected, the control PC 106 allows the beam emitted from the light source 201-2 to enter into the subject's eye 207. Specifically, a state where entry of the beams emitted from the light sources 201-1 and 201-2 into the subject's eye 207 is limited before the AOSLO measurement button 507 is selected is changed to a state where the beam emitted from the light source 201-1 enters into the subject's eye 207. This switching is carried out by the driving/control unit 114 by, for example, turning ON the turned-OFF light source 201-1 or opening the shutter 291-1 inserted into the optical path connecting the subject's eye 207 with the light source 201-1. Either one of the limitation of the entry of the beam emitted from the light source 201-3 into the subject's eye 207 and the permission of the entry of the beam emitted from the light source 201-1 into the subject's eye 207 may be executed first, or both may be simultaneously executed. However, it is desired that to limit the increase of a beam amount entered into the subject's eye 207 as much as possible, after the entry of the beam emitted from the light source 201-3 into the subject's eye 207 is limited, the entry of the beam emitted from the light source 201-1 into the subject's eye 207 is allowed.

When the aberration correction pause button 508 is selected, the control PC 106 temporarily stops aberration correction. For example, while the aberration determination unit 113 continues aberration correction, the control of the spatial light modulator 259 by the driving/control unit 114 is stopped. Alternatively, the aberration correction itself is stopped. A resume button may be provided, and the aberration correction may be resumed when the resume button is selected. Alternatively, when the aberration correction pause button 508 is selected again, the aberration correction may be resumed.

In the shutter state display region 509, information indicating opened/closed states of the shutters 291-1 to 291-3 is displayed by the display control unit 112. In the example illustrated in FIG. 7, for the shutters 291-1 to 291-3, regions indicating an opened state (illustrated as "OPEN" in FIG. 7) of the shutter and a closed state (illustrated as "CLOSE" in FIG. 7) of the shutter are formed. The regions are highlighted according to the opened/closed states of the shutters 291-1 to 291-3. For example, FIG. 7 illustrates an opened state of the shutter 291-1 and closed states of the shutters 291-2 and 291-3. However, the form of the shutter state display region 509 is not limited to this. Any other display forms may be employed as long as the opened/closed states of the shutters 291-1 to 291-3 can be confirmed. For example, switches corresponding to the shutters 291-1 to 291-3 may be displayed. In this case, the switch may be pressed when the shutter is opened while the switch may not be pressed when the shutter is closed.

In the aberration display region 511, the aberration determined (calculated) by the aberration determination unit 113 is displayed as a time-sequential graph by the display control unit 112.

In the anterior eye portion display region 512, the anterior eye portion image generated by the image generation unit 111 based on the output of the CCD camera 260 is displayed by the display control unit 112.

In the fixation lamp display region 513, information indicating a fixation position is displayed by the display control unit 112. For example, in the fixation lamp display region 513, a grid indicating fixation coordinates is displayed, and the fixation position is displayed, for example, as a bright spot on the grid. When a certain point on the grid is selected using the operation unit, the driving/control unit 114 changes a lighting position 265 in the fixation lamp 256 according to the selected position. In the fixation lamp display region 513, coordinates indicating a current fixation position may be displayed as numerical values. In this case, the lighting position 265 can be changed by changing the displayed numerical values.

In the wavefront display region 514, a Hartman image detected by the wavefront sensor 255 is displayed by the display control unit 112. The wavefront display region 514 may be always provided, or popped up as another window when the aberration measurement button 506 is selected, aberration measurement is started, and a Hartman image is obtained. The pop-up configuration enables the screen of the liquid crystal monitor 105 to be effectively used in a state where aberration is not being measured.

In the WFSLO display region 515, a WFSLO image generated by the image generation unit 111 is displayed by the display control unit 112.

In the WFSLO intensity display region 516, signal intensity of the WFSLO image is displayed by the display control unit 112. More specifically, the signal intensity of the WFSLO image is displayed as a time-sequential graph.

When the WFSLO recording button 517 is selected, the driving/control unit 114 records the WFSLO image in a storage unit (not illustrated) such as a hard disk drive (HDD).

In the AOSLO display region 518, an aberration-corrected AOSLO image is displayed by the display control unit 112.

In the AOSLO intensity display region 519, signal intensity of the AOSLO image is displayed by the display control unit 112. More specifically, the signal intensity of the AOSLO image is displayed as a time-sequential graph.

When the AOSLO recording button 520 is selected, the driving/control unit 114 records the AOSLO image in a storage unit (not illustrated) such as a HDD.

When the autofocus button 521 is selected, in the driving/control unit 114 automatically adjusts positions of the lenses 235-10, 235-14, 235-16, and 235-18 so that a defocus value becomes small.

When the aberration correction button 522 is selected, the driving/control unit 114 automatically adjusts the spatial light modulator 259 so that an aberration amount becomes smaller.

The imaging condition setting button 523 includes, for example, an imaging field angle setting button, a frame rate setting button, and an imaging time setting button. For example, the imaging field angle setting button includes a plurality of buttons corresponding to a plurality of field angles. The examiner can perform imaging with a desired filed angle by selecting a button corresponding to the desired field angle. The frame rate setting button and the imaging time setting button are configured as of the imaging field angle setting button.

The depth adjustment button 524 is, for example, a slider. The driving/control unit 114 drives the lens 235-10 according to a moving amount and a moving direction of the slider. The depth adjustment button 524 is not limited to the slider. Any other forms can be employed as long as the lens 235-10 can be driven.

In the aberration display region 525, an aberration amount of a defocus component (μm unit) and all aberration amounts (μm RMS unit) determined by the aberration determination unit 113 are displayed by the display control unit 112. Only one of these may be displayed. The units of the displayed aberration amounts are not limited to these units. Other units may be used.

Hereinafter, description will return to the flowchart of FIG. 6.

In step S2, when the execution button 501 on the control software screen is pressed, an image of the anterior eye portion is displayed in the anterior eye portion display region 512. When the center of a pupil is not correctly displayed at a screen center, the head portion 102 is moved to a roughly correct position by using the joystick 107. When further adjustment is necessary, the electric stage button 503 on the control screen is pressed, and the jaw receiver 108 is slightly moved by the driving/control unit 114.

Then, in step S22, the driving/control unit 114 opens the closed WFSLO shutter 291-2. In the shutter state display region 509, the opened state of the WFSLO shutter 291-2 is displayed. In the shutter state display region 509, closed states of the shutters 291-1 and 291-3 are displayed.

Timing of opening the WFSLO shutter 291-2 may be a timing when the execution button 501 of the control software screen is selected, when the control software is activated, or when the image of the anterior eye portion is displayed in the anterior eye portion display region 512.

In step S3, when the image of the anterior eye portion is displayed in a roughly correct state, a WFSLO image is displayed in the WFSLO display region 515. For example, the examiner sets the fixation lamp at a center position of a fixation lamp position display region 513, and guides a line of sight of the subject's eye 207 to the center position. For example, the WFSLO measurement button 505 is automatically selected when the control software is activated or when the execution button 501 is selected.

Then, watching intensity of the WFSLO image displayed in a WFSLO intensity display region 516, the examiner adjusts the focus adjustment button 504 to increase WFSLO intensity. In the WFSLO intensity display region 516, signal intensity detected by the WFSLO unit is time-sequentially displayed with a horizontal axis indicating time and a vertical axis indicating signal intensity. By adjusting the focus adjustment button 504, the positions of the lenses 235-10, 235-14, 235-16, and 235-18 are simultaneously adjusted by the driving/control unit 114.

When the WFSLO image is clearly displayed, the examiner presses the WFSLO recording button 517 to store WFSLO data (WFSLO image).

In step S4, the examiner checks the WFSLO image displayed in the WFSLO display region 515 and stored in step S3, and determines a position of obtaining an AOSLO image by a unit described below. Then, the examiner guides the line of sight of the subject's eye 207 so that the position can be set, for example, on the center of the WFSLO display region 515.

There are two units for determining the position of obtaining the AOSLO image: one is a method for instructing a position of the fixation lamp in a fixation lamp position display region 513, and the other is a method for clicking a desired position of the WFSLO image in the WFSLO image display region 515. A pixel in the WFSLO display region 515 and the position of the fixation lamp are associated with each other. The driving/control unit 114 automatically moves the position of the fixation lamp according to the clicked position to guide the line of sight of the subject's eye to a desired position. Since the line of sight of the subject's eye is guided by using the WFSLO image stored in step S3, it is not necessary to enter the beam emitted from the light source 201-2 to obtain the WFSLO image into the subject's eye during processing of step S4.

After confirming that the position of the AOSLO image to be obtained has moved to the center of the WFSLO display region 515, the processing proceeds to a next step. In the present exemplary embodiment, the region of obtaining the ALSLO image is a rectangular region of a predetermined size around the optical axis of the optical system illustrated in FIG. 2. In other words, the region of obtaining the ALSLO image is a rectangular region of a predetermined size around the center of the WFSLO display region 515. The region of obtaining the ALSLO image is not limited to this. The region can be arbitrarily changed.

The WFSLO image may be obtained again after the position of the fixation lamp is changed, and whether the desired position of the subject's eye 207 is at the center position of the WFSLO display region 515 may be confirmed to adjust the fixation position again. In this case, when entry of the measuring beam from the light source 201-3 into the subject's eye 207 is limited, the limitation is released to allow the measuring beam to enter into the subject's eye 207. Thus, the desired position of the subject's eye 207 can be surely moved to the center position of the WFSLO display region 515, and application time of the beam to the subject's eye 207 can be shortened.

In step S44, when the aberration measurement button 506 is selected, the driving/control unit 114 closes the shutter 291-2. Closing the shutter 291-2 limits (e.g., blocs off) entry of the beam emitted from the light source 201-2 into the subject's eye 207. In response to the storage of the WFSLO image, the driving/control unit 114 may close the shutter 291-2. In other words, step S44 may be carried out before step S4.

Then, in step S45, the driving/control unit 114 opens the shutter 291-3. Opening the shutter 291-3 allows the beam emitted from the light source 201-3 to enter into the subject's eye 207. For example, the fixation lamp 256 is in a lit state when the control software is activated or the execution button 501 is selected. In other words, the driving/control unit 114 serving as the control unit allows the first measuring beam to enter into the subject's eye in the entered state of the beam emitted from the fixation lamp into the subject's eye.

Further, the driving/control unit 114 performs display indicating the opened state of the shutter 291-3 and the closed states of the shutters 291-1 and 291-2 in the shutter state display region 509.

Then, in step S5, the display control unit 112 displays a Hartman image detected by the wavefront sensor 255 in a wavefront display region 514. The display control unit 112 displays aberration calculated from the Harman image in an aberration display region 511. The aberration is divided into a defocus component (μm unit) and all aberration amounts (μm RMS unit) to be displayed. Since the positions of the focus lenses 235-10 and 235-16 for the AOSLO measuring beam and the beacon beam have been adjusted in step S3, preparation has been made for aberration measurement at this step.

When the autofocus button 521 is pressed, the driving/control unit 114 automatically adjusts the positions of the lenses 235-10, 235-14, 235-16, and 235-18 to reduce the defocus value.

Then, when the aberration correction button 522 is pressed, the driving/control unit 114 adjusts the spatial light modulator 259 in a direction where an aberration amount becomes smaller, and the display control unit 112 displays a value of the aberration amount on the liquid crystal monitor 105 in real time. In step S6, the driving/control unit 114 compares the aberration amount with a predetermined threshold value. When the value of the aberration amount is equal to or smaller than the predetermined threshold value (0.03 μm RMS) (YES in step S6), the driving/control unit 114 automatically presses the AOSLO measurement button 507, and the processing proceeds to step S66. When the value of the aberration amount is not equal to or smaller than the predetermined threshold value (NO in step S6), the processing proceeds to step S5. In this case, the examiner may press the aberration correction pause button 508 to stop the aberration correction. Then, the processing proceeds to step S66 by pressing the AOSLO measurement button 507. The threshold value of the aberration amount is not limited to this threshold value. The threshold value can be arbitrarily set. When the aberration amount calculated by the aberration determination unit 113 is not equal to or lower than the threshold value for a predetermined time (NO in step S6), the AOSLO measurement button 507 may be automatically selected by the driving/control unit 114.

In step S66, when the value of the aberration amount is equal to or lower than the predetermined threshold value, the driving/control unit 114 closes the shutter 291-3. In other words, when the AOSLO measurement button 507 is selected, the driving/control unit 114 closes the shutter 291-3. Closing the shutter 291-3 limits (blocs off) entry of the beam emitted from the light source 201-3 into the subject's eye 207.

In step S66, when the shutter 291-3 is closed, the driving/control unit 114 opens the shutter 291-1 in step S67. In other words, when the AOSLO measurement button 507 is selected, the driving/control unit 114 opens the shutter 291-1. Opening the shutter 291-1 allows the beam emitted from the light source 201-1 to enter into the subject's eye 207. In other words, the driving/control unit 114 allows the second measuring beam to enter into the subject's eye after the entry of the first measuring beam into the subject's eye is limited from the state when the first measuring beam is entered into the subject's eye and the entry of the second measuring beam into the subject's eye is limited. In the shutter state display region 509, the opened state of the shutter 291-1 is displayed, and the closed states of the shutters 291-2 and 291-3 are displayed.

In step S7, an aberration-corrected AOSLO image is displayed in the AOSLO display region 518. In the AOSLO intensity display region 519, as in the case of the WFSLO intensity display region 516, signal intensity of the AOSLO image is time-sequentially displayed.

When the signal intensity is insufficient, watching the AOSLO intensity display region 519, the examiner adjusts a focus and a jaw reception position to increase the signal intensity.

By the imaging condition setting button 523, the examiner can designate an imaging field angle, a frame rate, and imaging time.

By adjusting the depth adjustment button 524 to move the lens 235-10, the examiner can adjust an imaging range of the subject's eye 207 in the depth direction. Specifically, by adjusting the depth adjustment button 524, an image of a desired layer such as a stratum neuroepitheliale retinae, a nerve fiber layer, or a pigmented layer can be obtained.

When the AOSLO image is clearly displayed, the examiner presses the AOSLO recording button 520 to store AOSLO data (AOSLO image). Then, the driving/control unit 114 limits entry of the measuring beam 206-1 into the subject's eye 207.

In step S77, after the AOSLO image is stored, the AOSLO shutter 291-1 is closed to limit entry of the measuring beam 206-1 into the subject's eye. In the shutter state display region 509, closed states of all the shutters 291-1 to 291-3 are displayed.

In step S8, the examiner determines whether to change the imaging position. When the imaging position is changed (YES in step S8), the processing returns to step S4. Step S44 after the return to step S4 is omitted. On the other hand, when the imaging position is not changed (NO in step S8), the processing proceeds to step S9. Supposing that an imaging position changing button is displayed on the liquid crystal display monitor 105, when this imaging position changing button is selected, the control PC 106 may determine that the imaging position will be changed. When the imaging position changing button is not selected for a predetermined time after the AOSLO image is, the control PC 106 may determine that the imaging position will not be changed.

In step S9, the examiner determines whether to switch left and right eyes. When the switching is to be carried out, the processing returns to step S2. On the other hand, when the left and right eyes are not to be switched (NO in step S9), the processing proceeds to step S10. Supposing that a left and right eye switching button is displayed on the liquid crystal display monitor 105, when this left and right eye switching button is selected, the control PC 106 may determine that a right eye will be switched. When the left and right eye switching button is not selected for a predetermined time after the AOSLO image is stored, the control PC 106 may determine that the right eye will not be switched. The execution order of step S8 and step S9 can be reversed.

In step S10, the examiner presses the stop button 502 to stop the control software. The control software is stopped, and the series of imaging operations is ended.

<Image Confirmation>

Next, referring to FIG. 8, a method for converting the data captured by the AOSLO apparatus of the present exemplary embodiment into an image to confirm it will be described.

Figure 8:
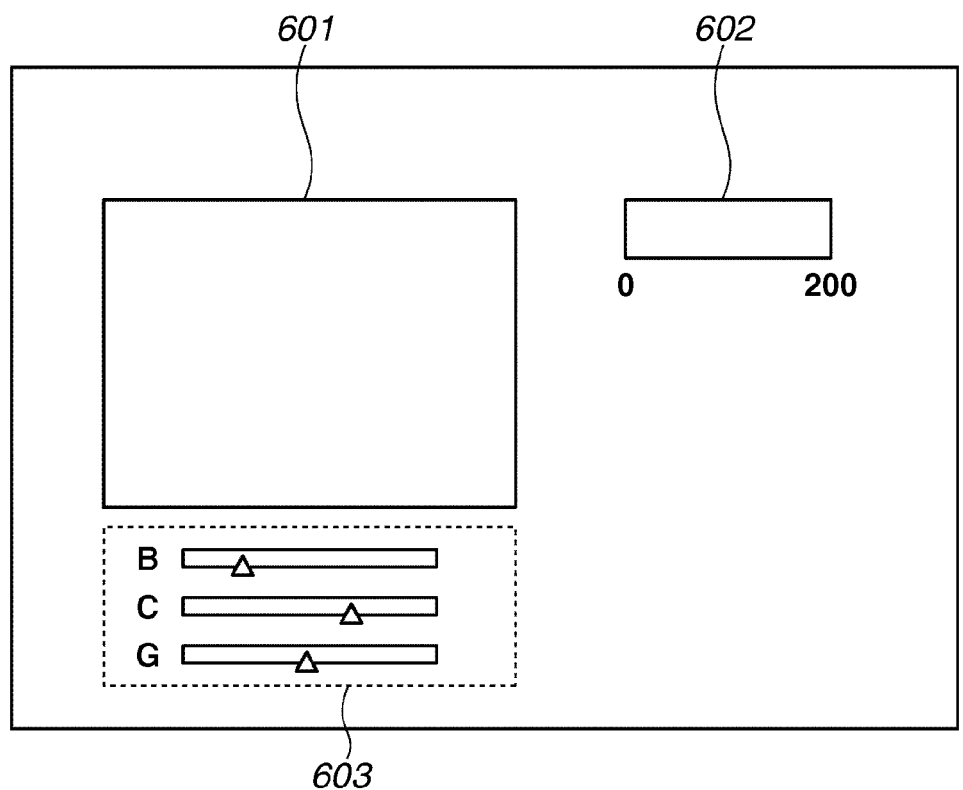
FIG. 8 illustrates an example of a configuration of an image browsing software screen of the AOSLO apparatus according to an exemplary embodiment of the present invention.

FIG. 8 illustrates an example of a configuration of an image browsing software screen according to the present exemplary embodiment.

When viewer software for visualizing image data captured by the software control unit 110 is activated, the display control unit 112 displays the image browsing software screen illustrated in FIG. 9 on the liquid crystal monitor 105.

This viewer software can read the stored WFSLO data or AOSLO data to form an image.

The viewer software screen includes an image display region 601, an image number selection unit 602, and an image quality adjustment unit 603.

In the image display region 601, an image selected by using the image number selection unit 602, such as an AOSLO image, is displayed. A WFSLO image corresponding to the AOSLO image may be displayed in the image display region 601 by providing a display switching unit such as a tab. Accordingly, the AOSLO image and the WFSLO image can be easily compared with each other in sight. Further, the AOSLO image and the WFSLO image may be displayed side by side.

The image number selection unit 602 is configured to select a desired AOSLO image from a plurality of AOSLO images obtained by the AOSLO apparatus 101. For example, the image number selection unit 602 is a slider. The position of the slider is associated with an image number of the AOSLO image. The examiner can select a desired AOSLO image by moving the slider via an instruction unit. The number of captured images varies depending on measuring time period, and image numbers are added in order of time. The image number selection unit 602 is not limited to the slider. A region to which the image number can be directly input may be employed.

The image quality adjustment unit 603 is a slider configured to adjust image brightness, contrast, and gamma (illustrated as "B", "C", and "G", respectively). Image quality can be adjusted by sliding the slider left and right. The control PC 106 can adjust quality of an image such as an AOSLO image based on an input to the image quality adjustment unit 603.

The viewer software screen is not limited to the example. For example, a fixation position when the AOSLO image displayed in the image display region 601 is obtained may be displayed as a coordinate value or a drawing. Coordinates of the face receiver 104 when the AOSLO image displayed in the image display region 601 is obtained may be displayed. Further, luminance or amplitude of the AOSLO image with respect to scanning time when the AOSLO image displayed in the image display region 601 is obtained may be displayed as a graph. Information indicating a position of at least one of the lenses 235-10, 235-14, 235-16, and 235-18 when the AOSLO image displayed in the image display region 601 is obtained may be displayed.

The AOSLO image may be displayed as a moving image in the image display region 601. In this case, values of the parameters such as the fixation position at the time of obtaining the AOSLO image corresponding to the AOSLO image are sequentially displayed.

Thus, according to the present exemplary embodiment, the AOSLO image can be obtained while simultaneously entering the beams into the subject's eye from the plurality of light sources. Thus, reduction of image quality can be prevented while securing safety.

In the entered state of the beam emitted from the light source 201-3 into the subject's eye 207, the fixation lamp 256 is turned ON. Thus, movement of the subject's eye 207 can be suppressed, and aberration measurement can be accurately performed.

By limiting entry of the measuring beam emitted from the light source 201-2 after storage of the WFSLO image into the subject's eye 207 and adjusting the obtaining position of the AOSLO image by using the WFSLO image, the beam amount applied to the subject can be reduced more.

According to the present exemplary embodiment, when the limitation of the entry of the measuring beam into the subject's eye 207 is released, time from turning-OFF of the light sources 201-1 to 201-3 to stable emission of the beam becomes unnecessary. Thus, reduction of image quality can be prevented while securing safety, and examination time can be prevented from being longer.

The beams emitted from the light sources 201-1 to 201-3 do not simultaneously enter into the subject's eye. Thus, each beam amount can be increased, and a highly accurate AOSLO image can be obtained.

Since the opened/closed states of the shutters 291-1 to 291-3 are displayed in the shutter state display region 509, the examiner can clearly and easily know which of the measuring beams 206-1 to 206-3 is being applied to the subject's eye 207. Thus, assuredness of the imaging operation is improved.

In the case of the AOSLO apparatus 101 of the present exemplary embodiment, suitable waveforms for usage are assigned to the respective light sources by arranging the light source for anterior eye portion observation, the light source for aberration measurement, the light source for AOSLO image acquisition, and the light source for WFSLO image acquisition in this order from the short wavelength side. Thus, according to the AOSLO apparatus 101 of the present exemplary embodiment, a highly accurate AOSLO image can be obtained. In other words, the highly accurate AOSLO image can be obtained by using a wavelength relationship among the light sources suitable for the AOSLO apparatus. According to the present exemplary embodiment, the wavelength determination method of each light source in the apparatus including the plurality of light sources is clarified. Further, according to the present exemplary embodiment, the wavelengths can be effectively used by setting the interval between the center wavelengths double or more of the sum of ½ of half-value full widths of the adjacent light sources. Conventionally, any method for determining wavelengths to effectively use the wavelengths has not been disclosed. However, as in the case of the present invention, when the interval between the center wavelengths is set double or more of the sum of ½ of half-value full widths of the adjacent light sources, unnecessary widening of the interval between the center wavelengths can be prevented, and the wavelengths can be effectively used according to sensitivity of the sensor or desired resolution. The present exemplary embodiment can be applied to an anterior eye.

The exemplary embodiment has been directed to the eyes. However, the present invention can be applied to other portions such as skins or organs.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™, a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-126193 filed Jun. 1, 2012, which is hereby incorporated by reference herein in its entirety.

What is claimed is:

1. An ophthalmologic apparatus comprising:
   a first light source configured to emit a first measuring beam;
   a second light source configured to emit a second measuring beam;
   a first limitation unit disposed in an optical path connecting the first light source with a subject's eye and configured to limit entry of the first measuring beam into the subject's eye;
   a second limitation unit disposed in an optical path connecting the second light source with the subject's eye and configured to limit entry of the second measuring beam into the subject's eye;
   an aberration measurement unit configured to measure aberration caused by a subject's eye by using a return beam of the first measuring beam from the subject's eye;
   a correction unit configured to correct aberration of the return beam of the second measuring beam from the subject's eye caused by the subject's eye based on the aberration measured by the aberration measurement unit;
   a first acquisition unit configured to obtain a first image of the subject's eye by using the aberration-corrected return beam of the second measuring beam from the subject's eye; and
   a control unit configured to allow, in lit states of the first light source and the second light source, one of the first measuring beam and the second measuring beam to enter into the subject's eye while limiting entry of the other measuring beam into the subject's eye by controlling the first limitation unit and the second limitation unit.

2. The ophthalmologic apparatus according to claim 1,
   wherein the first limitation unit and the second limitation unit are shutters; and
   wherein the control unit switches entry and entry limitation of the measuring beams into the subject's eye by controlling opening/closing of the shutters.

3. The ophthalmologic apparatus according to claim 2, wherein the display control unit causes the display unit to display opened/closed states of the shutters.

4. The ophthalmologic apparatus according to claim 1,
   wherein the first limitation unit and the second limitation unit are filters; and
   wherein the control unit switches entry and entry limitation of the measuring beams into the subject's eye by inserting/pulling out the filters into/from the optical paths.

5. The ophthalmologic apparatus according to claim 4, wherein the display control unit causes the display unit to display inserted/pulled-out states of the shutters.

6. The ophthalmologic apparatus according to claim 1, further comprising a display control unit configured to cause a display unit to display forms indicating incident states of the first measuring beam and the second measuring beam into the subject's eye.

7. The ophthalmologic apparatus according to claim 1, wherein the limitation unit allows the second measuring beam to enter into the subject's eye after the entry of the first measuring beam into the subject's eye is limited from a state where the first measuring beam is entered into the subject's eye and entry of the second measuring beam into the subject's eye is limited.

8. The ophthalmologic apparatus according to claim 1, further comprising a fixation lamp configured to guide a direction of a line of sight of the subject's eye,
wherein the control unit allows the first measuring beam to enter into the subject's eye in an entered state of a beam emitted from the fixation lamp into the subject's eye.

9. An ophthalmologic apparatus comprising:
a first illumination optical system configured to illuminate a subject's eye with a first measuring beam emitted from a first light source;
a second illumination optical system configured to illuminate the subject's eye by scanning the subject's eye with a second measuring beam emitted from a second light source;
a third illumination optical system configured to illuminate the subject's eye by scanning the subject's eye with a third measuring beam emitted from a third light source;
a first shutter disposed in the first illumination optical system;
a second shutter disposed in the second illumination optical system;
a third shutter disposed in the third illumination optical system;
a measurement optical system configured to measure aberration caused by the subject's eye by using a return beam of the first measuring beam from the subject's eye;
a first imaging optical system configured to capture an image of the subject's eye by using a return beam of the second measuring beam from the subject's eye;
a second imaging optical system configured to capture an image of the subject's eye by using a return beam of the third measuring beam from the subject's eye to determine an imaging position of the first imaging optical system;
a correction unit disposed in the first imaging optical system and configured to correct aberration of the return beam of the second measuring beam from the subject's eye by using the aberration measured by the measurement optical system; and
a control unit configured to control, in lit states of the first light source, the second light source, and the third light source, opening/closing of the first shutter, the second shutter, and the third shutter to open one of the first shutter, the second shutter, and the third shutter while closing the other two shutters.

10. An ophthalmologic apparatus comprising:
a first illumination optical system configured to illuminate the subject's eye by scanning the subject's eye with a first measuring beam emitted from a first light source;
a second illumination optical system configured to illuminate the subject's eye by scanning the subject's eye with a second measuring beam emitted from a second light source;
a first shutter disposed in the first illumination optical system;
a second shutter disposed in the second illumination optical system;
a measurement optical system configured to measure aberration caused by the subject's eye;
a first imaging optical system configured to capture an image of the subject's eye by using a return beam of the first measuring beam from the subject's eye;
a second imaging optical system configured to capture an image of the subject's eye by using a return beam of the second measuring beam from the subject's eye to determine an imaging position of the first imaging optical system;
a correction unit disposed in the first imaging optical system and configured to correct aberration of the return beam of the first measuring beam from the subject's eye by using the aberration measured by the measurement optical system; and
a control unit configured to control, in lit states of the first light source and the second light source, opening/closing of the first shutter and the second shutter to open one of the first shutter and the second shutter while closing the another shutter.

11. The ophthalmologic apparatus according to claim 10, wherein the display control unit causes the display unit to display opened/closed states of the first shutter and the second shutter.

12. An ophthalmologic apparatus comprising:
a first light source configured to emit a first measuring beam;
a second light source configured to emit a second measuring beam;
a first limitation unit disposed in an optical path connecting the first light source with a subject's eye and configured to limit entry of the first measuring beam into the subject's eye;
a second limitation unit disposed in an optical path connecting the second light source with the subject's eye and configured to limit entry of the second measuring beam into the subject's eye;
an aberration measurement unit configured to measure aberration caused by a subject's eye;
a correction unit configured to correct aberration of the return beam of the first measuring beam from the subject's eye caused by the subject's eye based on the aberration measured by the aberration measurement unit;
a first acquisition unit configured to obtain a first image of the subject's eye by using the aberration-corrected return beam of the first measuring beam from the subject's eye;
a second acquisition unit configured to obtain a second image of the subject's eye by using the return beam of the first measuring beam, the second image being used for determining an imaging position of the first image; and
a control unit configured to allow, in lit states of the first light source and the second light source, one of the first measuring beam and the second measuring beam to enter into the subject's eye while limiting entry of the other measuring beam into the subject's eye by controlling the first limitation unit and the second limitation unit.

13. The ophthalmologic apparatus according to claim 12,
wherein the first limitation unit and the second limitation unit are shutters, and
wherein the control unit switches entry and entry limitation of the measuring beams into the subject's eye by controlling opening/closing of the shutters.

14. The ophthalmologic apparatus according to claim 13, wherein the display control unit causes the display unit to display opened/closed states of the shutters.

15. A control method of an ophthalmologic apparatus having:
a first light source configured to emit a first measuring beam;
a second light source configured to emit a second measuring beam;
a first limitation unit disposed in an optical path connecting the first light source with a subject's eye and configured to limit entry of the first measuring beam into the subject's eye; and
a second limitation unit disposed in an optical path connecting the second light source with the subject's eye and configured to limit entry of the second measuring beam into the subject's eye,
the method comprising:
measuring aberration caused by a subject's eye by using a return beam of the first measuring beam from the subject's eye;
correcting aberration of the return beam of the second measuring beam from the subject's eye caused by the subject's eye based on the measured aberration;
obtaining a first image of the subject's eye by using the aberration-corrected return beam of the second measuring beam from the subject's eye; and
allowing, in lit states of the first light source and the second light source, one of the first measuring beam and the second measuring beam to enter into the subject's eye while limiting entry of the other measuring beam into the subject's eye by controlling the first limitation unit and the second limitation unit.

16. A control method of an ophthalmologic apparatus having:
a first light source configured to emit a first measuring beam;
a second light source configured to emit a second measuring beam;
a first limitation unit disposed in an optical path connecting the first light source with a subject's eye and configured to limit entry of the first measuring beam into the subject's eye; and
a second limitation unit disposed in an optical path connecting the second light source with the subject's eye and configured to limit entry of the second measuring beam into the subject's eye,
the method comprising:
measuring aberration caused by a subject's eye;
correcting aberration of the return beam of the first measuring beam from the subject's eye caused by the subject's eye based on the measured aberration;
obtaining a first image of the subject's eye by using the aberration-corrected return beam of the first measuring beam from the subject's eye;
obtaining a second image of the subject's eye by using the return beam of the first measuring beam, the second image being used for determining an imaging position of the first image; and
allowing, in lit states of the first light source and the second light source, one of the first measuring beam and the second measuring beam to enter into the subject's eye while limiting entry of the other measuring beam into the subject's eye by controlling the first limitation unit and the second limitation unit.

\* \* \* \* \*